US010589250B2

(12) United States Patent
Schopf et al.

(10) Patent No.: US 10,589,250 B2
(45) Date of Patent: Mar. 17, 2020

(54) AUTOMATED PURIFICATION AND FORMULATION DEVICE FOR RADIOPHARMACEUTICAL COMPOUNDS

(71) Applicants: THE REGENTS OF THE UNIVERSITY OF CALIFORNIA, Oakland, CA (US); SOFIE BIOSCIENCES, INC., Culver City, CA (US)

(72) Inventors: Eric Schopf, Los Angeles, CA (US); Melissa Moore, Beverly Hills, CA (US); R. Michael van Dam, Los Angeles, CA (US); Brandon Maraglia, Los Angeles, CA (US); Alexander Hsiao, Los Angeles, CA (US)

(73) Assignees: THE REGENTS OF THE UNIVERSITY OF CALIFORNIA, Oakland, CA (US); SOFIE BIOSCIENCES, INC., Culver City, CA (US)

( * ) Notice: Subject to any disclaimer, the term of this patent is extended or adjusted under 35 U.S.C. 154(b) by 199 days.

(21) Appl. No.: 15/698,350

(22) Filed: Sep. 7, 2017

(65) Prior Publication Data
US 2018/0065103 A1     Mar. 8, 2018

Related U.S. Application Data

(60) Provisional application No. 62/384,490, filed on Sep. 7, 2016.

(51) Int. Cl.
*B01J 19/00*     (2006.01)
*B01J 19/24*     (2006.01)
(Continued)

(52) U.S. Cl.
CPC ............. *B01J 19/004* (2013.01); *B01J 19/24* (2013.01); *A61K 2121/00* (2013.01);
(Continued)

(58) Field of Classification Search
CPC ........ B01J 19/004; B01J 19/08; B01J 19/081; B01J 2219/00759; B01J 2219/00925; C07B 59/00; C07B 59/002; C07B 59/005
See application file for complete search history.

(56) References Cited

U.S. PATENT DOCUMENTS

| 7,586,102 B2 | 9/2009 | Mourtada et al. |
| 7,897,935 B2 | 3/2011 | Karpinski |

(Continued)

FOREIGN PATENT DOCUMENTS

| JP | 2009-047454 A | 3/2009 |
| KR | 10-2013-002795 A | 3/2013 |
| WO | 2014/160799 A1 | 10/2014 |

OTHER PUBLICATIONS

Alauddin, Mian M. et al., Synthesis of [18F]-labeled adenosine analogues as potential PET imaging agents, J Label Compd Radiopharm 2003; 46: 805-814.

(Continued)

*Primary Examiner* — Jill A Warden
*Assistant Examiner* — Dwayne K Handy
(74) *Attorney, Agent, or Firm* — Vista IP Law Group LLP

(57) ABSTRACT

A device for purifying and formulating a radiopharmaceutical compound includes an automated purification subsystem that automates the loading of a sample into a sample loop for downstream purification via HPLC. A column selector valve is provided to select from one of a plurality of columns. Fractions can be collected as well as the desired product. The device includes an automated formulation subsystem that first sends the product to a dilution reservoir (Continued)

prior to being pneumatically pushed onto a solid phase extraction (SPE) cartridge. Automated rinse, elution, and reconstitution are also performed with the automated formulation subsystem. The device may be directly coupled to the output of an automated radiosynthesizer.

20 Claims, 16 Drawing Sheets

(51) Int. Cl.
 G21G 4/08 (2006.01)
 G21G 1/00 (2006.01)
 G21F 7/04 (2006.01)
(52) U.S. Cl.
 CPC ............ B01J 2219/00164 (2013.01); B01J 2219/00191 (2013.01); G21F 7/04 (2013.01); G21G 1/0005 (2013.01); G21G 4/08 (2013.01)

(56) References Cited

U.S. PATENT DOCUMENTS

| | | |
|---|---|---|
| 2006/0245980 A1 | 11/2006 | Kiselev et al. |
| 2012/0108858 A1 | 5/2012 | Kiselev |
| 2013/0020727 A1 | 1/2013 | Klausing et al. |
| 2016/0280734 A1 | 9/2016 | Moore |

OTHER PUBLICATIONS

Alauddin, Mian M. et al., Synthesis of [18F]-labeled 72'-deoxy-2'-fluoro-5-methyl-1-B-D-arabinofuranosyluracil([18F]-FMAU), J Label Compd Radiopharm 2002; 45: 583-590.
Anderson, Harry et al., Improved synthesis of 2'-deoxy-2'[18F]-fluoro-1-B-D-arabinofuranosyl-5-iodouraci ([18F]-FIAU), Nuclear Medicine and Biology 37 (2010) 439-442.
Cai, Hangcheng et al., The improved synthesis of 5-substituted 2'[18F]fluoro-2'-deoxy-arabinofuranosyluracil derivatives ([18F]FEAU, [18F]FFAU, [18F]FCAU, [18F]FBAU and [18F]FIAU) using a multistep one-pot strategy, Nuclear Medicine and Biology 38 (2011) 659-666.
Chin, Frederick T. et al., Semiautomated Radiosynthesis and Biological Evaluation of [18F]FEAU: A Novel PET Imaging Agent for HSV1-tk/sr39tk Reported Gene Expression, Mol Imaging Biol (2008) 10:82-91.
Coenen, H.H. et al., Fluorine-18 radiopharmaceuticals beyong [18F]FDG for use in oncology and neurosciences, Nuclear Medicine and Biology 37 (2010) 727-740.
Herman, Henry et al., Multi-pot radiosynthesizer capable of high-pressure reactions for production of [18F]FAC and analogs, J. Nucl Med. 2011; 52 (Supplement 1):1440.
Herman, Henry et al., Flexible radiosynthesizer capable of multi-pot high temperature and pressure reactions, Crump Institute Molecular Imaging, UCLA, Department of Molecular & Medical Pharmacology, UCLA, Sofie Biosciences, Inc. (PPT) (2011) (24pages).
Herman, Henry et al., Flexible radiosynthesizer capable of multi-pot high temperature and pressure reactions, Crump Institute Molecular Imaging, UCLA, Department of Molecular & Medical Pharmacology, UCLA, Sofie Biosciences, Inc. (Abstract) (2011) (1page).
Keng, Pei Yuin et al., Emerging Technologies for Decentralized Production of PET Tracers, Positron Emission Tomography—Current Clinical and Research Aspects, www.intechopen.com, InTech; 2012; 153-182.
Li, Zibo et al., Automated synthesis of 2'-deoxy-2'-[18F]fluoro-5-methyl-1-B-D-arabinofuranosyluracil ([18F]-FMAU) using a one reactor radiosynthesis module, Nuclear Medicine and Biology 38 (2011) 201-206.
Moore, Melissa D. et al., ARC-P HS+: A versatile radiosynthesizer for the production of PET tracers, AACR Annual Meeting, Mar. 31-Apr. 4, 2012, Chicago, IL (1page).
Paolillo, Vincenzo et al., A fully automated synthesis of [18F]-FEAU and [18F]-FMAU using a novel dual reactor radiosynthesis module, J. Label Compd. Radiopharm 2009, 52, 553-558.
Sachinidis, John I et al., Automation for Optimised Production of Fluorine-18-Labelled Radiopharmaceuticals, Current Radiopharmaceuticals, 2010, 3, 248-253.
PCT International Search Report for PCT/US2014/031905, Applicant: The Regents of the University of California, Form PCT/ISA/210 and 220, dated Jul. 25, 2014 (5pages).
PCT Written Opinion of the International Search Authority for PCT/US2014/031905, Applicant: The Regents of the University of California,, Form PCT/ISA/237, dated Jul. 25, 2014 (5pages).
PCT International Preliminary Report on Patentability (Chapter I of the Patent Cooperation Treaty) for PCT/US2014/031905, Applicant: The Regents of the University of California, Form PCT/IB/326 and 373, dated Oct. 8, 2015 (7pages).
Ackermann, Uwe et al., Fully automated synthesis and coupling of [18F]FBEM to glutathione using iPHASE FlexLab module, J. Label Compd. Radiopharm 2014, 57, 115-120.
Ackermann, Uwe et al., Synthesis of F-18 Fluoroestradiol Using the Flexlab Radiosynthesizer, Centre for PET, Austin Hospital, Studley Road, Melbourne VIC 3084, Australia, Ludwig Institute for Cancer Research, Melbourne Centre for Clinical Sciences, Eastern Heal, Box Hill Hospital, undated, (1page).
Claggett, Shane B et al., Simplified programming and control of automated radiosynthesizers through unit operations, EJNMMI Research 2013, 3:53 (13pages).
Goh, Yit Wooi et al., Fully automated Click radiolabeling for [18F]FLETT and the synthesis and coupling of [18F]FBEM to glutathione using the iPHASE FlexLab module, Centre for PET, Austin Health, Heidelberg, Australia, The University of Melbourne, Australia, Ecole Nationale Superieure de Chimie de Rennes, France, IPHASE technologies, Australia, undated, (1page).
Patt, Marianne et al., Fully automated radiosynthesis of both enantiomers of [18F]Flubatine under GMP conditions for human application, Applied Radiation and Isotopes 80 (2013) 7-11.
Explora FM, Explora FM Formulation Module, http://www.siemens.com, Siemens Healthcare Limited-2017—(1page).
Product Description and Specification, Catalog No. 4, Syntra RNplus Research, Synthra GmbH, Albert-Einstein-Ring 21, D-22761 Hamburg, Germany (2015).

US 10,589,250 B2

AUTOMATED PURIFICATION AND FORMULATION DEVICE FOR RADIOPHARMACEUTICAL COMPOUNDS

RELATED APPLICATION

This Application claims priority to U.S. Provisional Patent Application No. 62/384,490 filed on Sep. 7, 2016, which is hereby incorporated by reference in its entirety. Priority is claimed pursuant to 35 U.S.C. § 119 and any other applicable statute.

STATEMENT REGARDING FEDERALLY SPONSORED RESEARCH AND DEVELOPMENT

This invention was made with Government support under Grant Nos. 2R44MH097271, R21AG049918, and HHSN261201400041C, awarded by the National Institutes of Health. The Government has certain rights in the invention.

TECHNICAL FIELD

The technical field generally relates to devices and methods used in the automated preparation of radiopharmaceuticals including Positron Emission Tomography (PET) probes.

BACKGROUND

The advent of molecular imaging approaches such as Positron Emission Tomography (PET) has enabled measurements of molecular and cellular mechanisms throughout the body in preclinical and clinical settings. Such measurements have widespread diagnostic utility and their use for evaluation of treatment responses and to assist drug development is expanding rapidly. Probes are traditionally synthesized by skilled radiochemists using specialized equipment and facilities that reduce their radiation exposure when working with large quantities of short-lived isotopes necessary to produce a final dose sufficient for imaging a human. In recent years, the development of automated radiosynthesizers that can produce a variety of different probes with minimal human intervention or radiation exposure has aimed to simplify routine synthesis of PET probes, especially for the clinic. As such, these synthesizers can be operated by technicians and do not require a highly trained radiochemist. Additionally, some automated systems can be configured to prepare different PET probes and thus also act as valuable tools for researchers developing new synthesis protocols for novel probes.

For example, the ELIXYS radiosynthesizer (Sofie Biosciences, Inc., Culver City, Calif.) is a disposable cassette-based, automated multi-reactor radiosynthesizer that is designed for both the development of new synthesis protocols as well as routine clinical and pre-clinical probe production. While synthesis operations for PET probes have been automated, once the probe has been produced, the final product that is injected into the subject often requires subsequent purification and formulation to remove or reduce exposure to potentially toxic organic solvents and chemical impurities. In some synthesis operations, the output of automated synthesizers is coupled to an entirely different purification system (e.g., high performance liquid chromatography HPLC) that is run by its own separate automated control system. After purification, formulation and concentration of the PET probe is performed manually using, for example, bulky rotary evaporation equipment. FIG. 1 illustrates a sequence of operations used to generate an injectable PET tracer according to the prior art. Thus, users had to employ multiple different types of systems to produce a final, injectable product. Not only is this expensive but it also means that users have to switch between different control systems for the various sub-systems, and the equipment takes up valuable space within the lead-shielded hot cell where the radiochemistry takes place. Different computers and control software are needed for each process making the overall automation process more complicated and expensive.

SUMMARY

In one embodiment, a device for purifying and formulating a radiopharmaceutical compound such as a PET tracer including an automated purification subsystem and an automated formulation subsystem. These two subsystems are contained or housed within a single device and are controlled using a computer controller that interfaces with the device. In one embodiment, the controller is the same controller that is used to control operations of the radiosynthesizer. The purification subsystem is used to take a crude radioactive product that has been generated from a radiosynthesizer and load the same into a sample loop (ins some embodiments one of a plurality of loops) using an automated HPLC injection valve. The crude product in the sample loop is delivered to one of a plurality of columns after passing through a column selector valve. After separation in the column, the product components (e.g., product, contaminants, residual reactants) are detected using an in-line UV detector and radiation detector. A computer controlled downstream fraction collection valve is actuated to pass these fractional components to waste, one or more fraction collection containers (e.g., tubes or vials), or a product output line.

The automated formulation subsystem includes a dilution reservoir that receives the fraction or product contained in the product output line (i.e., the product that is to be formulated). The diluted fraction or product is pushed onto a solid-phase extraction (SPE) cartridge using a compressed source of inert gas that enters the dilution reservoir. The fraction or product becomes trapped on the sorbent material (e.g., resin) contained therein while the liquid in which the product is dissolved passes through the resin and into a waste container. A multi-port syringe pump is provided that includes an output line that connects to a computer controlled cartridge valve that is located upstream of the SPE cartridge. The pump is used to first rinse the SPE with water to remove impurities or organic solvents. Next, using a different input port of the pump, an eluting liquid such as ethanol is aspirated and then pumped through the SPE cartridge to release the trapped product. In one embodiment, the eluted fluid that contains the fraction or product of interest is transferred to a final product container (e.g., a vial). Next, the pump then pumps a saline or other aqueous solution through the SPE cartridge and into the final product container for reformation (e.g., to ensure that ethanol content is below the allowable limit). The radiopharmaceutical compound contained in the final product container is ready for use.

According to one embodiment of the invention, a device for purifying and formulating a radiopharmaceutical compound such as a PET tracer includes an automated purification subsystem that includes a computer controlled injection valve coupled to a high performance liquid chromatography (HPLC) pump, a plurality of sample loops, and an output line from the injection valve, the computer controlled injection valve having one or more ports configured to receive an input fluid containing the radiopharmaceutical compound, wherein one of the plurality of sample loops is connected to the HPLC pump and the output line from the injection valve and another sample loop is connected to the port configured to receive the input fluid. An automated column selector valve is coupled to the output line from the injection valve and is configured to select one of a plurality of columns for fluid to pass through. The output from the column goes first through a UV detector and a radiation detector to a downstream fraction selector valve that is located downstream of the detectors and configured to divert fluid flow to one of a product output, waste output, and fraction output.

The device also includes an automated formulation subsystem coupled to an output of the downstream fraction selector valve that contains the desired product to be formulated. The automated formulation subsystem includes a dilution reservoir configured to receive the product fraction from the downstream fraction selector valve, the dilution reservoir being fluidically coupled to a solid-phase extraction cartridge. A computer controlled pump (e.g., syringe pump) is coupled to a plurality of different fluid reagents that include a wash solution, a saline solution, and an eluting solution, the computer controlled pump configured to pump selected the fluid reagents through the solid-phase extraction cartridge via a computer controlled cartridge valve interposed between the dilution reservoir and the solid-phase extraction cartridge. A final output line is fluidically coupled to the output of the solid-phase extraction cartridge, wherein a computer controlled waste valve is located downstream of the solid-phase extraction cartridge and can select between directing the fluid path to waste or to a final product container. Product is first trapped in the SPE cartridge which is then followed by rinsing the SPE cartridge with water. The trapped product is then eluted off of the SPE cartridge using an eluting liquid. This eluted product may be transferred to a final product container which can then be reformulated by passing a saline or other aqueous solution into the final product container. Alternatively, the eluted product may be transferred back to the automated radiosynthesizer for subsequent chemical reactions. In the latter configuration, the device for purifying and formulating a radiopharmaceutical compound is used as an intermediate step in the chemical synthesis.

In another embodiment, a system for the formation, purification, and formulation of a radiopharmaceutical compound is disclosed that includes a radiosynthesizer device configured for synthesizing radiopharmaceutical compound, an automated purification subsystem, an automated formulation subsystem, and a computer accessible controller interfacing the with the radiosynthesizer device, the automated purification subsystem, and the automated formulation subsystem, wherein one or more operations of the automated purification subsystem, the automated formulation subsystem, and the controller are programmable by a user.

The automated purification subsystem includes a computer controlled injection valve coupled to a high performance liquid chromatography (HPLC) pump, one or more sample loops, and an output line from the injection valve, the computer controlled injection valve having one or more ports configured to receive an input fluid containing the radiopharmaceutical compound from the radiosynthesizer device, wherein one of the sample loops is connected to the HPLC pump and the output line. An automated column selector valve is coupled to the output line from the injection valve and configured to select one of a plurality of columns to be used for sample purification. The column output is then directed into one or more detectors (e.g., a UV detector and radiation detector) for sample detection. A downstream fraction selector valve is configured to divert fluid flow to one of a product output, waste output, and fraction output. The fractions that are collected can be used by the chemist or operator to determine, for example, elution times for various products. The fractions may also be used to analyze product purity. Fractions can also be analyzed for new probe development. Fraction analysis is also used to tailor or optimize the conditions for separation of the desired products contained in the sample.

The automated formulation subsystem is coupled to the product output of the downstream fraction selector valve and includes a dilution reservoir configured to receive a product fraction from the downstream fraction selector valve, the dilution reservoir fluidically coupled to a solid-phase extraction cartridge. A compressed source of inert gas is coupled to the dilution reservoir via an automated valve, wherein the compressed source of inert gas pushes fluid contents contained in the dilution reservoir into the solid-phase extraction cartridge in response to actuation of the automated valve. A computer controlled pump (e.g., syringe pump) is coupled to a plurality of different fluid reagents and configured to pump selected fluid reagents through the solid-phase extraction cartridge via a computer controlled cartridge valve interposed between the dilution reservoir and the solid-phase extraction cartridge. A final output line is fluidically coupled to an output of the solid-phase extraction cartridge, wherein a computer controlled waste valve is coupled to the final output line to divert fluid flow to waste or the final output line. A computer accessible controller interfaces the with the radiosynthesizer device, the automated purification subsystem, and the automated formulation subsystem, wherein one or more operations of the automated purification subsystem, the automated formulation subsystem, and the controller are programmable by a user.

Product is trapped in the SPE cartridge followed by rinsing with water. The trapped product is then eluted off of the SPE cartridge using an eluting liquid. This eluted product may be transferred to a final product container which can then be reformulated by passing a saline or other aqueous solution into the final product container. The final product may also be transferred back into the radiosynthesizer instrument for additional chemical synthesis steps (e.g., intermediate purification).

DETAILED DESCRIPTION OF THE ILLUSTRATED EMBODIMENTS

Figure 1:
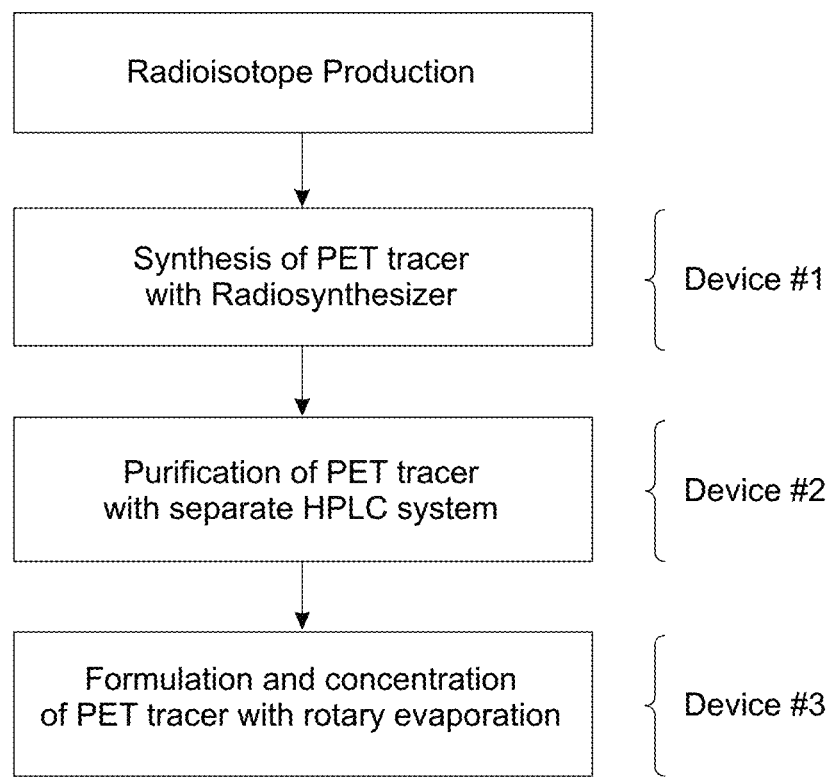
FIG. 1 illustrates a process for the formulation and concentration of a PET tracer according to the prior art.
Figure 2:
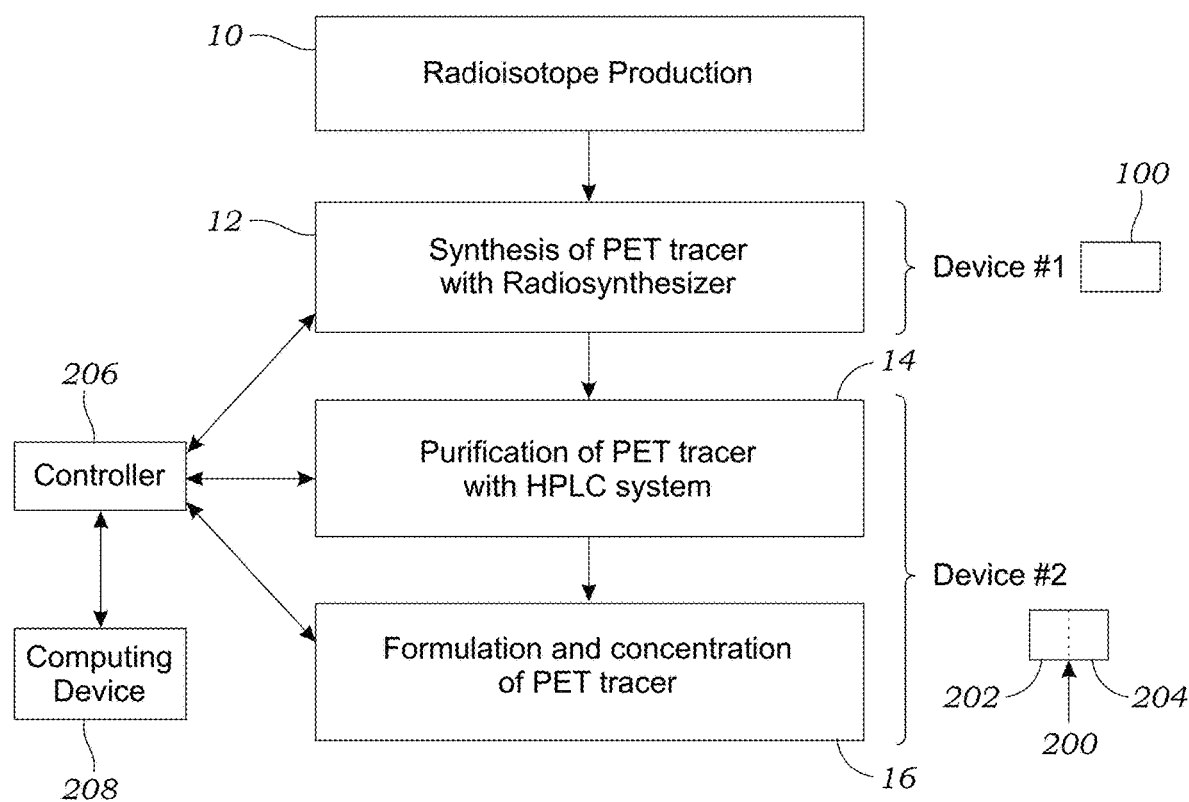
FIG. 2 illustrates a process for the formulation and concentration of a PET tracer according to one embodiment of the invention.

FIG. 2 illustrates an overview of a process for the formulation and concentration of a radiopharmaceutical compound (e.g., PET tracer) according to one embodiment of the invention. As seen in FIG. 2 a radioisotope is first generated or produced as seen in operation 10. The radioisotope is typically generated in a nuclear reactor, cyclotron, or generator. These radioisotopes may be produced on-site or ordered from a third party vendor. There are hundreds of radioisotopes that are used for medical applications. Of particular interest for medical imaging applications is the radioisotope fluorine-18 (F-18), which has become a key radioisotope that is used for cancer diagnosis, treatment evaluation, as well as a tool for research into cancer biology and drug development. Carbon-11 is another example of a radioisotope used in medical imaging applications (C-11). It should be understood, however, that the invention describe herein may be used with any number of radioisotopes. Next, as seen in operation 12, a radiopharmaceutical compound such as a PET tracer is synthesized using a radiosynthesizer 100 (illustrated in FIG. 3). The radiosynthesizer 100 is typically an automated device that is used to perform the chemical synthesis operations that are needed to generate the desired radiopharmaceutical compound. The radiosynthesizer 100 contains the reagents needed to generate the radiopharmaceutical compound as well as the flow paths, chemical reaction and other sites needed during the synthesis process. This includes, for example, modules or specific fluid pathways or sites for dispensing reagents, drying or evaporating products, transferring reagents or products, mixing reagents or products, reacting reagents or intermediate products, trapping, eluting, and the like. One example, of such a radiosynthesizer 100 is the ELIXYS radiosynthesizer 100 available from Sofie Biosciences (Culver City, Calif.) which is multi-reactor radiosynthesizer 100 that provides the user to perform one, two, or three pot synthesis. The ELIXYS radiosynthesizer 100 utilizes a reagent delivery robot for liquid handling and disposable cassettes 102 (FIG. 3) that provide a housing for all wetted flow paths. The ELIXYS radiosynthesizer 100 utilizes an intuitive graphical user interface which enables drag-and-drop unit operations to be performed according to the synthesis protocol being used. The ELIXYS radiosynthesizer 100 is described, for example, in Claggett et al., Simplified programming and control of automated radiosynthesizers through unit operations, EJNMMI Research, 3: 53 (2013) and in U.S. Patent Application Publication No. 2016/0280734, which are incorporated by reference herein. As seen in FIG. 2, the radiosynthesizer 100 is typically its own separate device (i.e., Device #1). While the radiosynthesizer 100 and the purification and formulation device 200 are illustrated as being two separate devices or modules that coordinate and work together, in another alternative embodiment, the functionality of the radiosynthesizer 100 and the purification and formulation device 200 may be incorporated into a single device.

Still referring to FIG. 2, according to the invention, a separate purification and formulation device 200 is provided that includes functionality to purify and formulate the radiopharmaceutical compound that is generated from radiosynthesizer 100. Typically, the radiosythesizer 100 generates a final product that contains contaminants, unreacted products, undesirable solvents and the like that need to be removed prior to use in mammals (e.g., humans). For example, radiopharmaceutical compounds are often produced in organic solvents such as acetonitrile, which is toxic above certain concentrations. Prior to being used in the human body, acetonitrile must be brought down to acceptable levels. Similar toxicity profiles exist for other organic solvents and reagents used in the production of radiopharmaceutical compounds. Purification is also needed to remove unwanted radioactive compounds that could interfere with the imaging process.

With reference to FIG. 2, according to the invention, the purification and formulation device 200 is provided that includes both a purification subsystem 202 as well as a formulation subsystem 204 that purifies the radiopharmaceutical compound to remove unwanted chemical byproducts or reactants as well as, in some embodiments, formulate a final solution that that contains the radiopharmaceutical compound that is ready for use in a mammal. For example, formulation may include reducing the concentration of ethanol (EtOH) to allowable levels through the dilution with saline or other aqueous solution. It may also include the addition of compounds that are used to adjust and/or stabilize pH, increase solubility, protect against radiolysis, etc. As seen in FIG. 2, this purification and formulation device 200 (i.e., Device #2) performs purification of the radiopharmaceutical compound using HPLC as seen in operation 14 followed by formulation and concentration of the radiopharmaceutical compound as illustrated in operation 16. As seen in FIG. 2, according to the invention, controller 206 is provided for the control of both the radiosynthesizer 100 and the purification and formulation device 200. As explained below, using a single computing device 208 that interfaces with the controller 206, a user is able to control and program not only the synthesis operations of the radiosynthesizer 100 but also the operations of the purification and formulation subsystems 202, 204.

Figure 3:
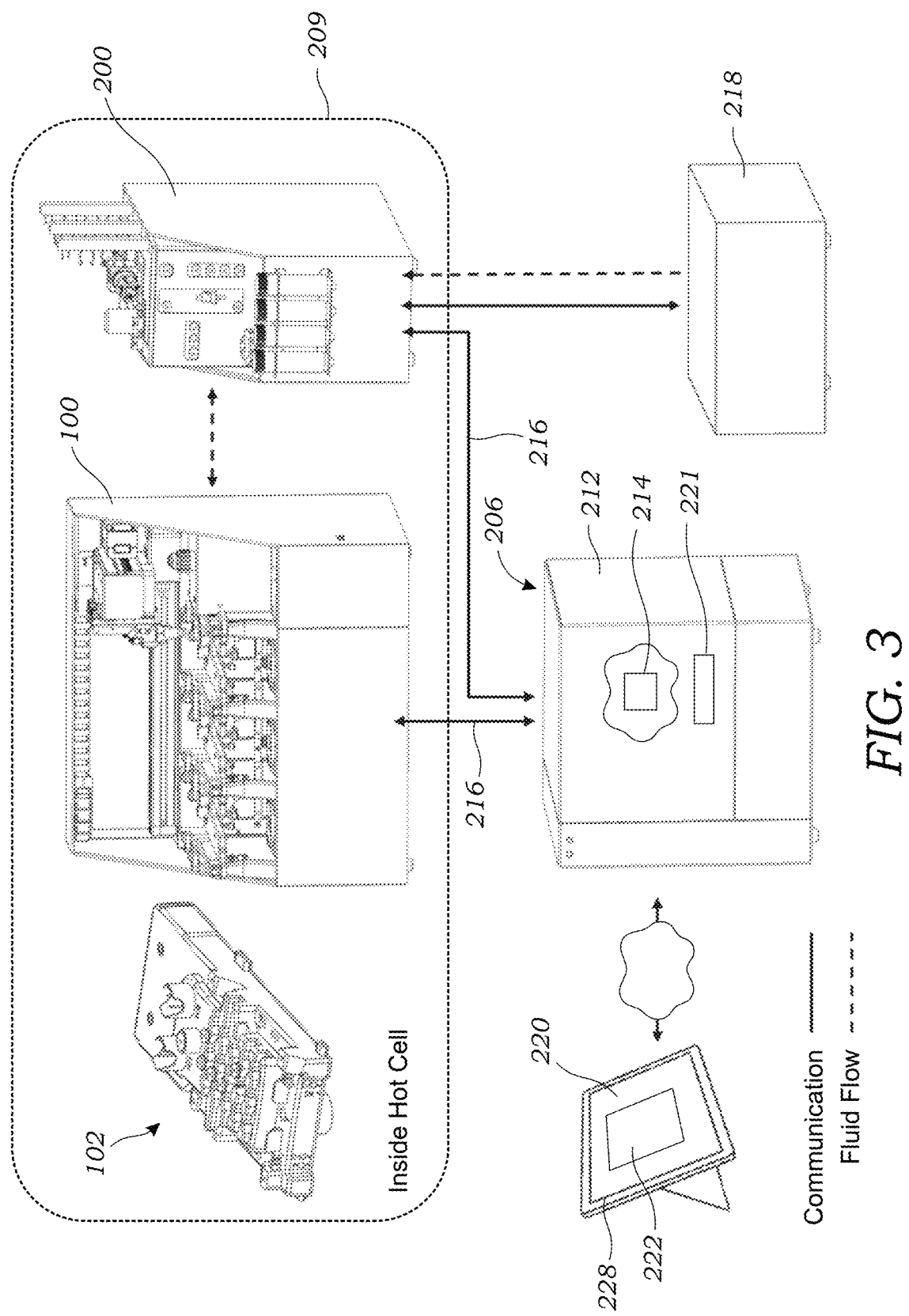
FIG. 3 illustrates a complete system that incorporates a radiosynthesizer, purification and formulation device (connected to an HPLC pump), and common controller. Also illustrated is a computing device that runs software thereon that is used, in conjunction with software contained on the controller, to control, program, and view data generated by the radiosynthesizer device and the purification and formulation device.

FIG. 3 illustrates the integration of the radiosynthesizer 100 and the purification and formulation device 200 through the use of a single controller 206. As seen in FIG. 3, both the radiosynthesizer 100 and the purification and formulation device 200 are located inside a hot cell 209. A hot cell 209 is a radiation shielded enclosure or working area that contains components that are in contact with radioactive materials. The controller 206 is located outside of the hot cell 209. The controller 206 includes a housing 212 that contains an embedded computer 214 that drives or operates the various subsystems of both the radiosynthesizer 100 and the purification and formulation device 200 using software 221. This includes, for example, driving the linear actuators, pneumatics, cooling, heating, HPLC injection, cameras, and radioactivity detectors of the radiosynthesizer 100. In addition, this includes, as explained herein, controlling the valves, pneumatics, sensors, pumps, and camera that are used in the purification and formulation device 200. The controller 206 interfaces with the radiosynthesizer 100 and the purification and formulation device 200 via data cables 216. These may include Ethernet cables and video cables when cameras are integrated into the radiosynthesizer 100 and the purification and formulation device 200.

FIG. 3 further illustrates an HPLC pump 218 that interfaces fluidically with the purification and formulation device 200. The HPLC pump 218, as explained below, is used to push the generated radiopharmaceutical compound from the radiosynthesizer 100 through the purification and formulation device 200 for purification using various liquid mobile phases (e.g., up to four (4) mobile phases may be used in many HPLC pumps). Control of the HPLC pump 218 is also controlled by the controller 206 via its interface with the purification and formulation device 200. The HPLC pump 218 may be located external to the hot cell 209 (FIG. 3), internal to the hot cell 209, or located within the purification and formulation device 200. FIG. 3 further illustrates a computing device 208 that is used by the operator to interface with the controller 206. The computing device 208 may include a personal computer, laptop, tablet pc, mobile phone, or the like. The computing device 208 contains software 220 located thereon that is used by the operator to access software 221 that is run from the embedded computer 214 to select the operations to be performed by the radiosynthesizer 100 and/or the purification and formulation device 200.

Typically, software 220 that includes a graphical user interface (GUI) 222 is provided on the computing device 208 so that the user can easily program the unit operations that are to be performed by the radiosynthesizer 100 and/or the purification and formulation device 200. Unit operations refer to those fundamental or building block operations that are employed the radiochemical synthesis process. Examples of unit operations include: ADD (for adding a reagent to a reaction vessel); EVAPORATE (for evaporating the contents of a reaction vessel); TRANSFER (for transferring the contents of one reactor to a next reactor; for transfer to an HPLC loop; or for transfer to the HPLC loop on the purification and formulation device 200); REACT (seals the reactor vessel to underside of disposable cartridge and heats); PROMPT (pauses sequence run and prompts the user); MOVE (moves a reactor to the front position for reaction vessel removal and/or installation and prompts the user); TRAPF18 (e.g., traps [$^{18}$F]Fluoride on a quaternary methylammonium (QMA) cartridge); ELUTEF18 (uses a reagent to elute [$^{18}$F]Fluoride off a QMA cartridge); MIX (mixes the contents of a reactor by stirring); EXTERNAL-ADD (allows the user to externally add a reagent via tubing); PURIFICATION (purification of one or more columns in the purification and formulation device 200); FORMULATION (which includes four steps of (1) FORMULATION: TRAP to trap the diluted radiopharmaceutical compound on the attached SPE cartridge 252, (2) FORMULATION: RINSE to rinse the trapped compound, (3) FORMULATION: ELUTE to elute the trapped compound, and (4) FORMULATION: RECONSTITUTE which adds saline and other additives, if appropriate, to the final product to reconstitute for administration).

As seen in FIG. 3, the computing device 208 may connect wirelessly (or wired) to the controller 206 using a wireless router or other connection (not shown) typically used to connect electronic devices in a wireless manner. For example, computing device 208 may connect to the controller 206 using a secure wireless Wi-Fi network or Bluetooth® connection. The software 221 that is executed on the controller 206 that is accessed by the computing device 208 may, in some embodiments, be an application or "app" 220 that is executed on the device 208. These types of application are common on tablet computers and mobile phone devices. The unit operations and their sequence are programmed by the user (e.g., by sequencing serial operations or selecting from pre-set operations) which are then executed by the controller 206 and electronics board 310 to control various computer controlled valves, pumps, and other components including, but not limited to, liquid sensors 274, 276, injection valve 240, column selector valve 242, UV detector 300, radiation detector 302 and amplifier 304, cartridge valve 316, waste valve 318, cleaning valve 320, pressure release valve 324, pressure regulator 400 set-points, syringe pump 306, and camera 314.

Figure 4:
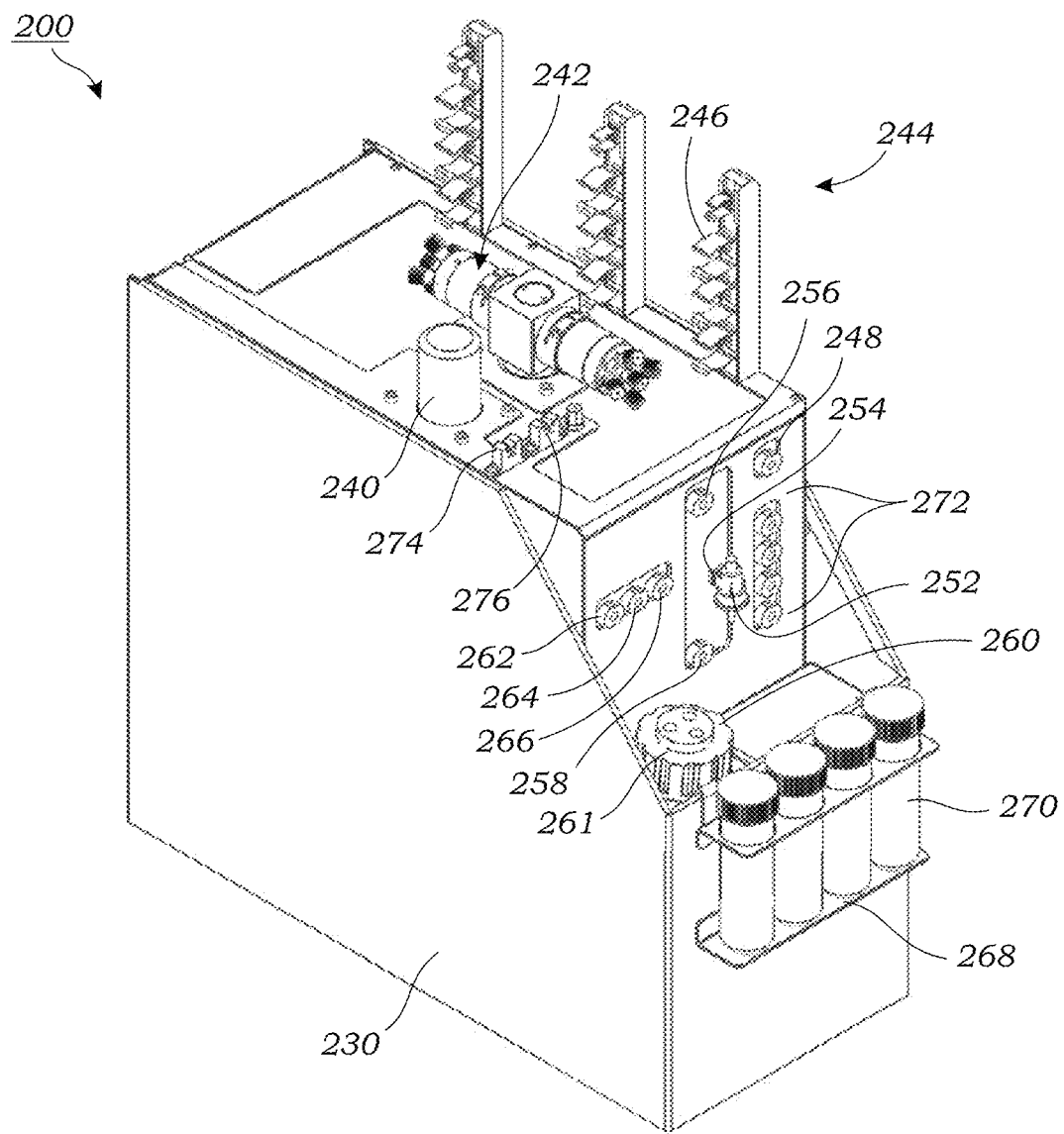
FIG. 4 illustrates a perspective view (front) of the purification and formulation device according to one embodiment.
Figure 5:
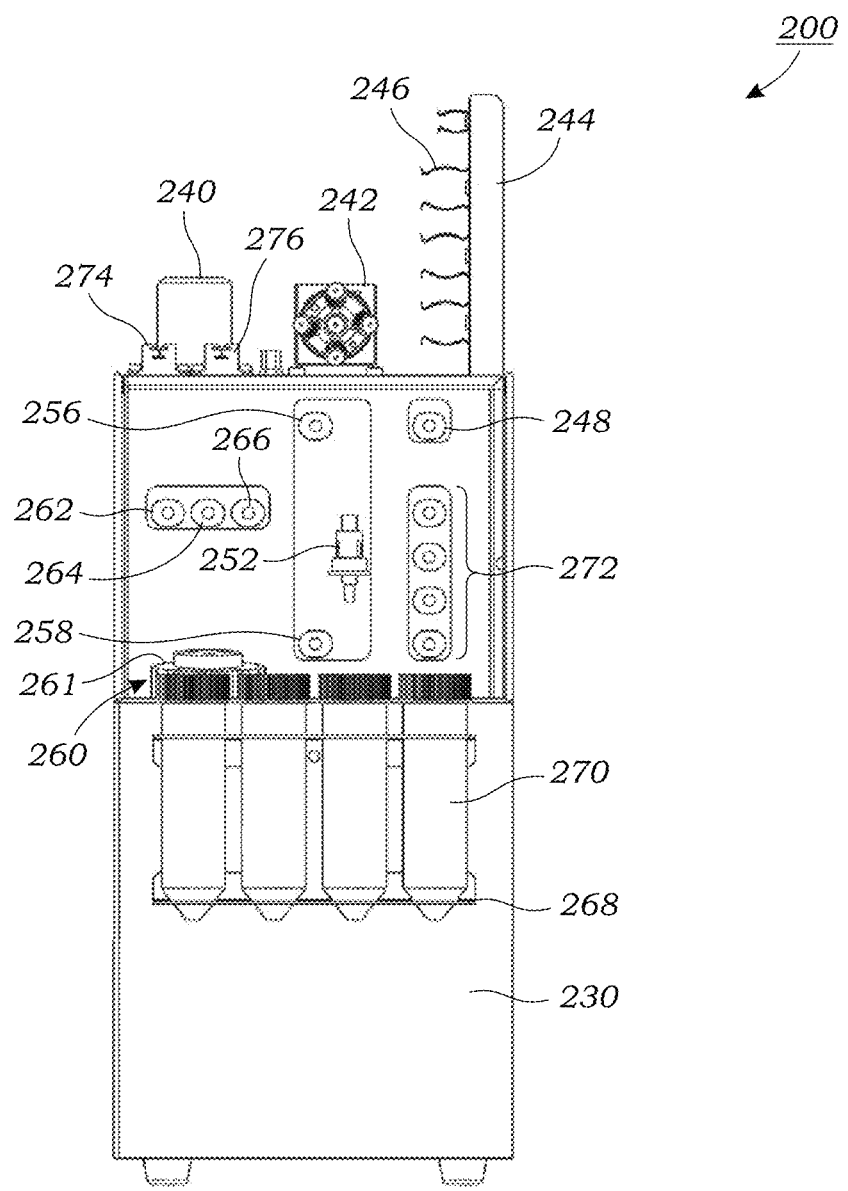
FIG. 5 illustrates a front view of the purification and formulation device of FIG. 4.
Figure 8:
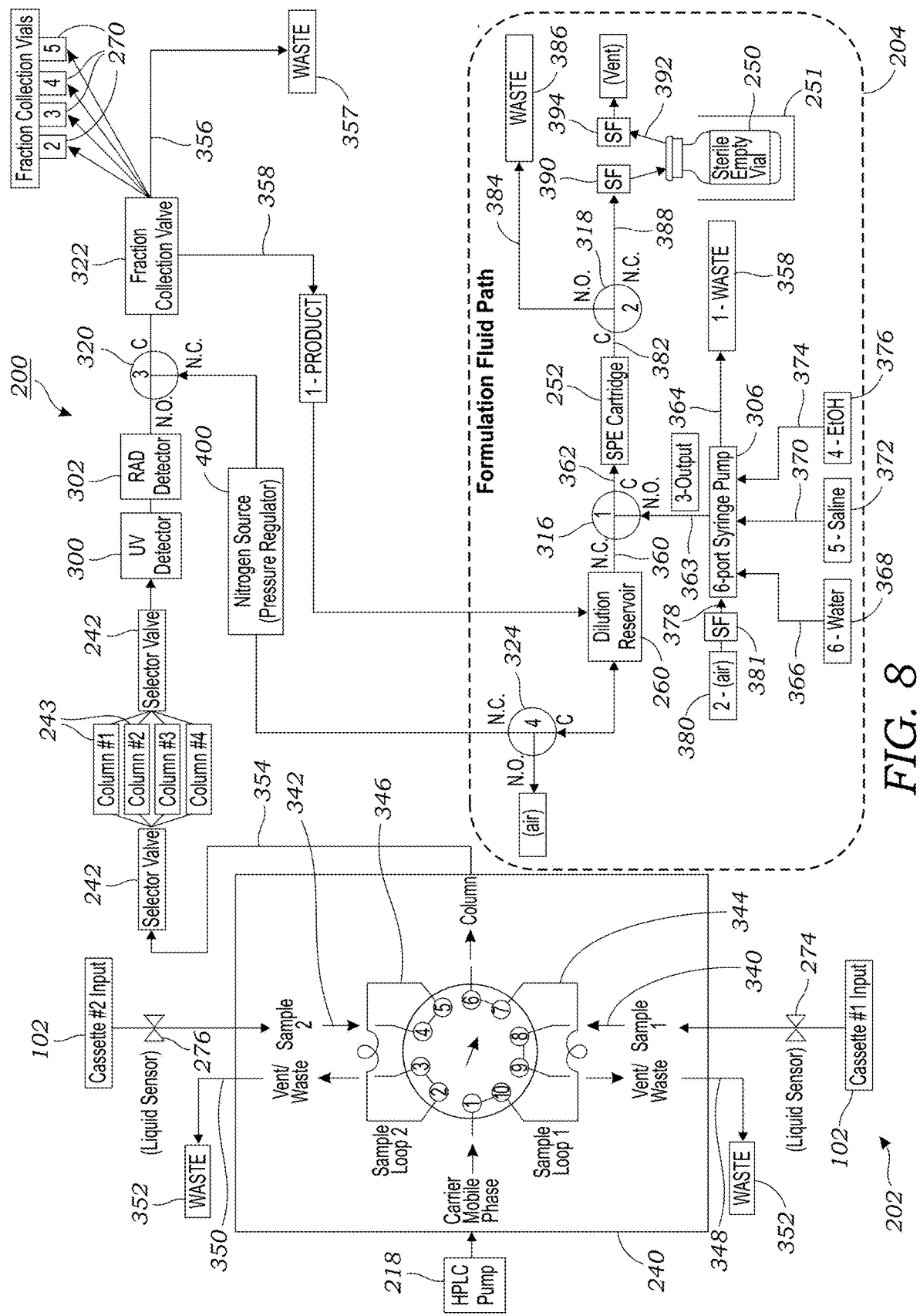
FIG. 8 illustrates a schematic layout of the flow paths in the purification and formulation device. N.O. for the valves stands for "normally open." N.C. stands for "normally closed." C stands for common or the common fluid pathway.

FIG. 4 illustrates a perspective view of the purification and formulation device 200. FIG. 5 illustrates a front facing view of the purification and formulation device 200. The purification and formulation device 200 is contained within a housing 230 that can be positioned in the hot cell 209 adjacent to radiosynthesizer 100. The output line of the radiosynthesizer 100 which is typically polymer tubing is connected to the injection valve 240 of the purification and formulation device 200 via input lines coupled to cassettes 102. For example, FIG. 8 illustrates two such input lines 340, 342 which may also referred to as "output" lines from the radiosynthesizer 100.

Figure 9:
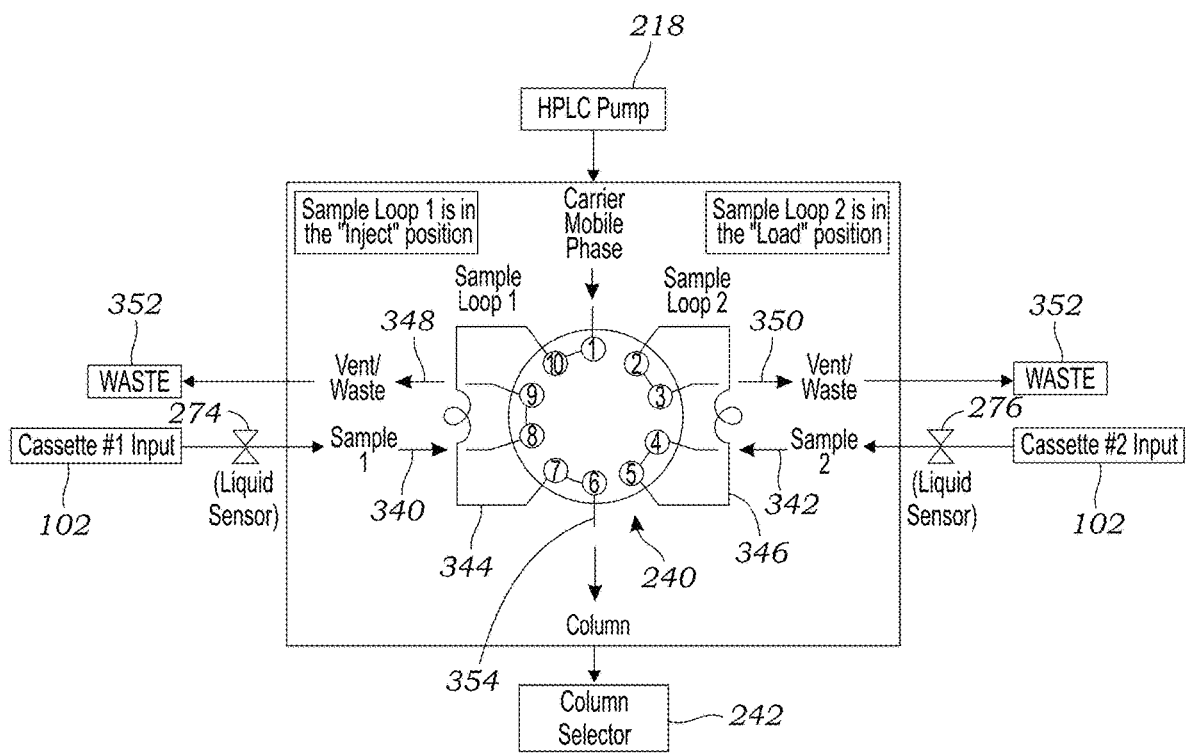
FIG. 9 illustrates an enlarged view of the injection valve of FIG. 8.

As used herein, "line" or "lines" refers to a conduit such as tubing that is used to carry fluid from one point to another. Lines can be metallic (e.g., stainless steel) as well as polymer tubing (e.g., ⅛ inch or 1/16 inch O.D. Teflon tubing). The injection valve 240, as explained in more detail herein, contains ten (10) ports with one of the ports being connected to the output line of the radiosynthesizer 100. As best seen in FIG. 9, two of the ports are connected to a first sample loop 344 while another two ports are connected to a second sample loop 346. Two additional ports on the injection valve 240 lead to waste lines 352. Another port is coupled to the HPLC pump 218. The remaining two ports on the injection valve 240 are connected to the outputs from the radiosynthesizer 100 (which serve as input lines 340, 342 to the purification and formulation device 200). For example, outputs from two different cassettes 102 are connected to injection valve 240. The injection valve 240 is a bi-state valve and is used to change the position of flow paths. As explained herein, actuation of the injection valve 240 toggles the configuration of the sample loops 344, 346 between an "injection" position and a "load" position.

Referring back to FIG. 4, the column selector valve 242 is used to select, during any particular purification run, one of a plurality of columns 243 (FIG. 8) that are held in a column holder 244 is affixed housing 230. The column holder 244 contains clips 246 that are used to hold the individual columns 243 in place. Stainless steel or another type of tubing (e.g., PEEK) is used to connect the output of the injection valve 240 to the column selector valve 242. Likewise, stainless steel or another type of tubing connects the ports on the column selector valve 242 to the individual columns 243. The column selector valve 242 includes pre-column valve components as well as post-column valve components that actuate pre and post column flow paths to selectively place the desired column 243 in the flow path.

Also illustrated in FIG. 4 is a final product output fitting 248 that is used to connect to flexible tubing that either leads to a final product container 250 (as seen in FIGS. 8, 10-13) in one embodiment or, in another embodiment, leads back to the radiosynthesizer 100. This latter configuration is for when an intermediate product may need to be purified and reacted further (e.g., mid-synthesis purification). The intermediate product may undergo purification and then sent back to the radiosynthesizer 100 for additional unit operations (e.g., reactions). The fittings described herein are typically flangeless nut fittings or flangeless ferrule fittings which are commonly used for pressurized fluid applications. A SPE cartridge 252 is illustrated secured to the face of the formulation device 200 using a clip 254. Fluid flows through the SPE cartridge 252 via fittings 256, 258. FIG. 4 also illustrates the dilution reservoir 260 along with corresponding dilution reservoir fittings 262, 264, 266. Each of these fittings serves a different function. One fitting 262 is used to deliver a product fraction to the dilution reservoir 260 (i.e., product in). Another fitting 264 is used for air vent and also to deliver compressed gas (e.g., nitrogen) to the dilution reservoir 260 to push fluid out of the dilution reservoir 260 for downstream formulation operations. Another fitting 266 connected to a tube which extends to the bottom of the dilution reservoir 260 is used to retrieve diluted product from the dilution reservoir 260 (i.e., product out). The dilution reservoir 260 includes a removable cap 261 that includes corresponding ports or fittings that corresponding to dilution reservoir fittings 262, 264, 266 and tubing which extends into the dilution reservoir 260. Also illustrated in FIG. 4 is a fraction tube holder 268 and can hang from the housing 230 and hold fraction tubes 270. Vials could also be used in place of fraction tubes 270. The fraction tubes 270 are used to collect different fractions obtained after passing through the column 242 and out one of the fraction fittings 272 (four (4) are illustrated but different numbers may be used). In another embodiment, the outputs from the fraction fittings 272 coupled to the fraction collection valve 322 may themselves be used to route products back to the radiosynthesizer 100 for intermediate purification and further reactions. While a compressed, inert gas is used to push fluid out of the dilution reservoir 260 in a preferred embodiment, air could also be used to push fluid out of the dilution reservoir 260. The air could be compressed or it may be contained in a syringe or other pumping device that can be actuated to displace liquid in the dilution reservoir 260.

Figure 6:
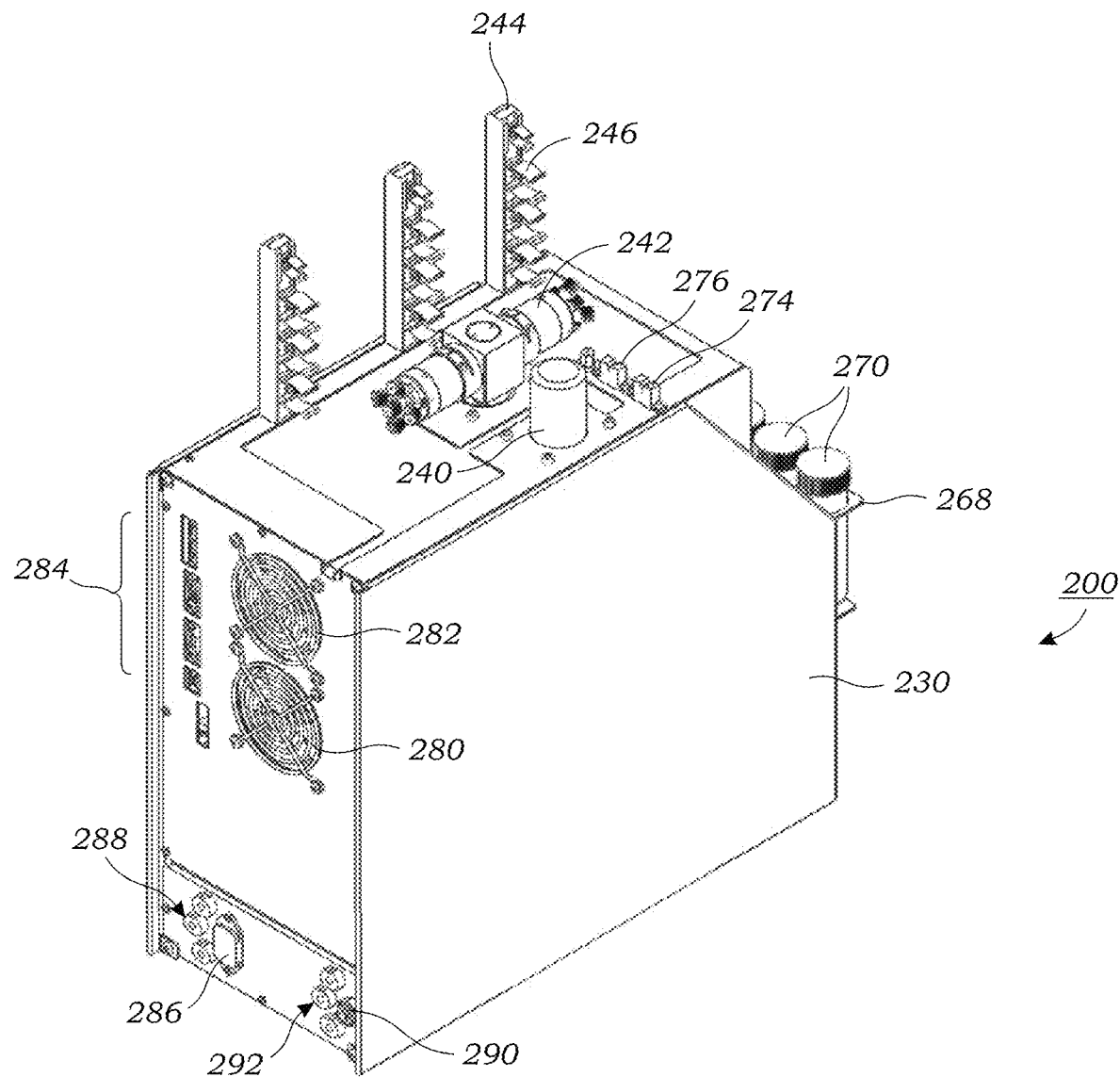
FIG. 6 illustrates another perspective view (rear) of the purification and formulation device of FIG. 4.

FIGS. 4 and 5 also illustrate liquid sensors 274, 276. These liquid sensors 274, 276 are used to detect the presence (or absence) of liquid in the two outputs from the radiosynthesizer 100. Flexible polymer tubing which connects the respective cassette 102 outputs from the radiosynthesizer 100 is placed in each respective sensor 274, 276. FIG. 6 illustrates a perspective view of the back side of the purification and formulation device 200. Two fans 280, 282 are mounted to the housing 230 and are used to cool the interior electronic and other heat generating components (e.g., UV sensor 300). Electronic input/output ports 284 are located on the back face of the housing 230 and are used to connect to the internal control electronics via the electronics board 310 including, for example, a video I/O port, HPLC pump port, Ethernet port, etc. A switchable power input 286 is provided which connects the purification and formulation device 200 to conventional source of A/C power. Three syringe pump inputs or fittings 288 are also provided which connect to inputs used for the syringe pump (e.g., water, saline solution, eluting solution) as described herein. An inert gas input 290 is located on the back face of the housing 230 and is connected to a source of inert gas such as nitrogen. Three waste ports or fittings 292 are also located on the back face of the housing 230 and connect to flexible tubing (not shown) that leads to waste container(s).

Figure 7:
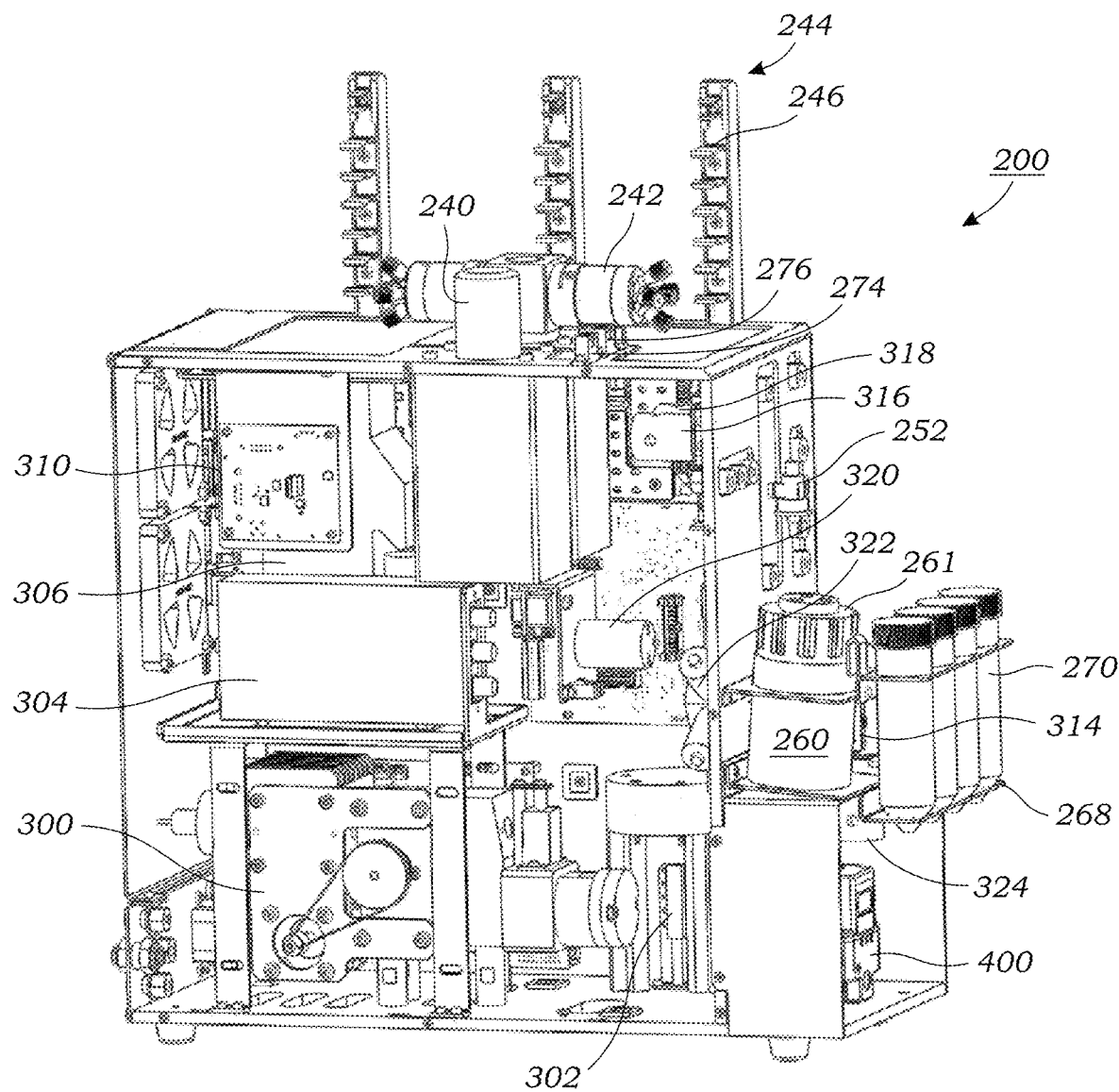
FIG. 7 illustrates an interior view of the purification and formulation device with a portion of the housing removed.
Figure 14:
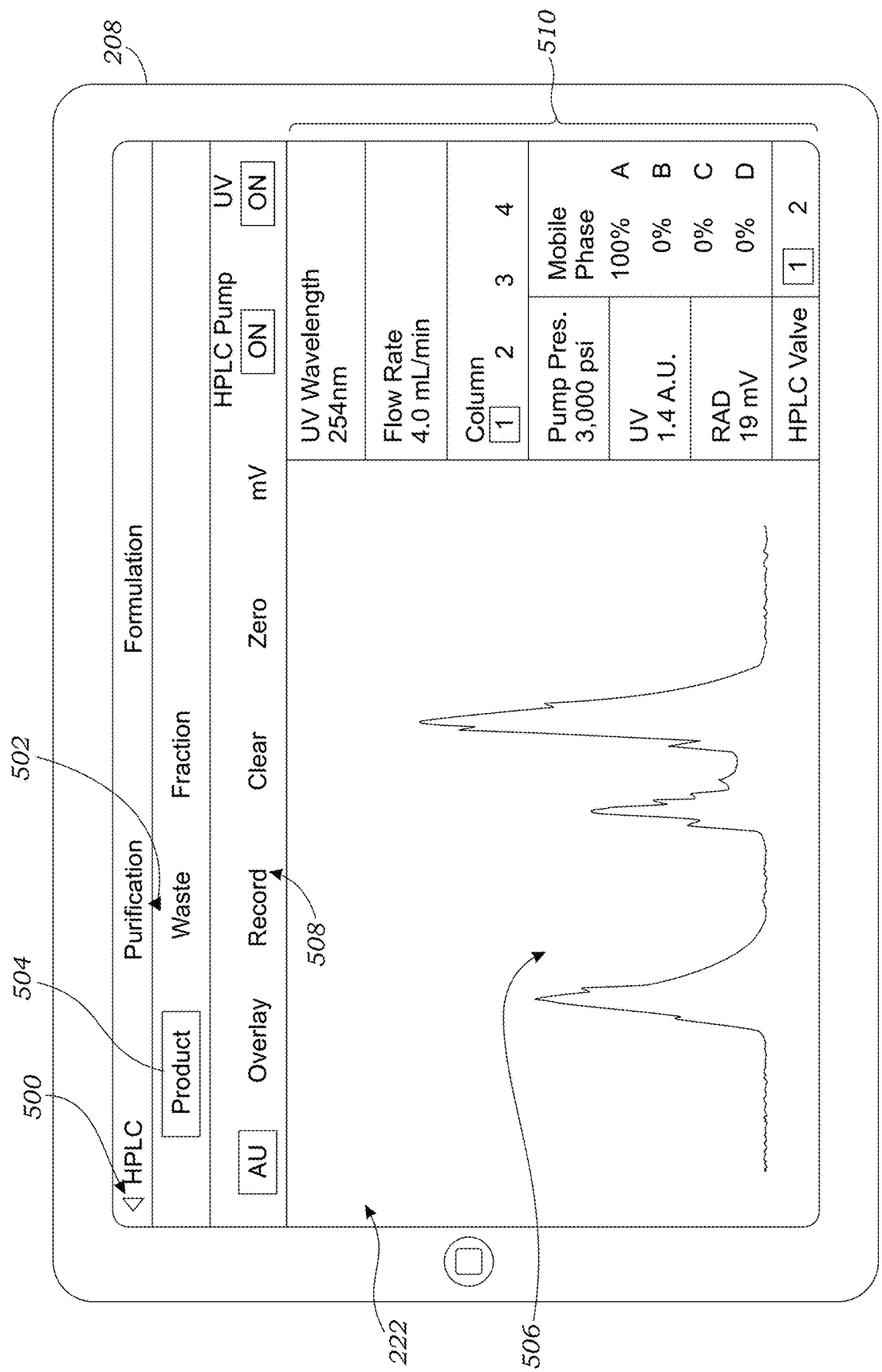
FIG. 14 illustrates an example of the GUI that is displayed to the user on the computing device that is used to program, control, and analyze data generated by the devices described herein.

FIG. 7 illustrates an interior view of the purification and formulation device 200 with a portion of the housing 230 removed. Located inside the purification and formulation device 200 is a UV detector 300. The UV detector 300 monitors product after traveling through the HPLC column 243. The UV detector 300 can monitor the absorbance of the product(s) passing through polymer tubing at one wavelength between 200 nm and 800 nm. Data from the UV detector 300 is transmitted to the controller 206 and then to the computing device 208 where data can be displayed to the user using the graphical user interface 222 as seen in FIG. 14. A radiation detector 302 is located immediately downstream of the UV detector 300 (with respect to flow path) and measures gamma rays emitted by the decaying radioisotope. A radiation detector 302 amplifier 304 is also located in the purification and formulation device 200 that is used to amplify the signal from the radiation detector 302. Like the data from the UV detector 300, data from the radiation detector 302 is transmitted to the controller 206 and then displayed on the graphical user interface 22 of the computing device 208. Additional detectors could also be incorporated into the flow path. These include, for example, sensors that measure refractive indices, conductivity, and pulsed amperometric detectors (for non-radioactive species).

A syringe pump 306 is also located in the purification and formulation device 200 and is used during the formulation operations. The syringe pump 306 is a six (6) port syringe pump that includes an output port, waste port, one input air port (for pushing residual eluting fluid through the lines when the output of the purification and formulation device 200 returns back to the radiosynthesizer 100), and three fluid input ports. One port is coupled via a fluid line to container or reservoir (e.g., Falcon tube) that holds water, another is coupled via a fluid line to a container or reservoir that holds saline, and the final input is coupled via a fluid line to a container or reservoir that holds the eluting fluid. These containers or reservoirs may be located outside of the purification and formulation device 200.

An electronics board 310 is also located in the in the purification and formulation device 200 and is used to interface with and control the various sub-systems including the liquid sensors 274, 276, injection valve 240, column selector valve 242, UV detector 300, radiation detector 302, cartridge valve 316, waste valve 318, cleaning valve 320, pressure release valve 326, pressure regulator 400, syringe pump 306, camera 314. Commands and data are communicated with the controller 206 using an Ethernet cable or other communication cable which carries data communications and a video cable that carries the video feed from the camera 314 to the controller 206. The information is read by the software 221 contained on the controller 206 and is then communicated with the computing device 208 for displaying data or assisting the user in making decisions using the GUI 222.

Figure 15:
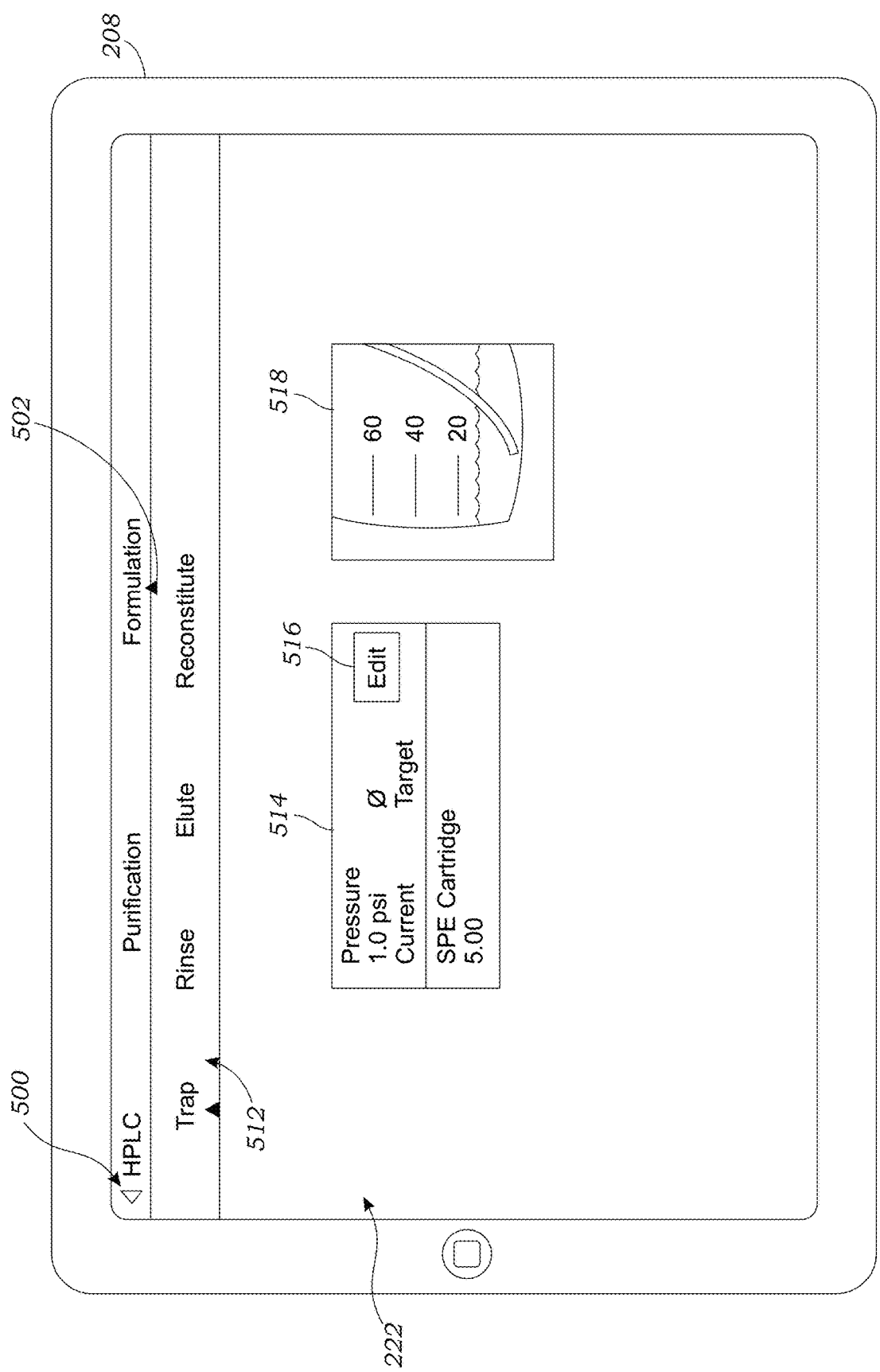
FIG. 15 illustrates an example of the GUI when the formulation subsystem functionality has been selected by the user.

A pressure regulator 400 is located in the in the purification and formulation device 200 and is used to regulate the pressure of the inert gas (e.g., nitrogen) that is used to push product from the dilution reservoir 260 during the formulation process as well as being used for cleaning operations. A camera 314 is located in the purification and formulation device 200 and is used to generate live video the dilution reservoir 260 which is then transmitted via the controller 206 to the computing device 208 and user interface 222 for viewing (FIG. 15). The camera 314 is focused on the bottom of the dilution reservoir 260 and indicates to the user how much fluid remains in the reservoir. In some concentration and formulation processes, the user may want to ensure that the dilution reservoir 260 has the appropriate amount of fluid and is not fully exhausted which may damage the trapped probe no the SPE cartridge 252.

A series of valves 316, 318, 320, 322, 324 are located in the purification and formulation device 200 and are used to divert various flow paths as described in more detail below. These include a cartridge valve 316 that is used during the formulation process to deliver fluid containing the product from the dilution reservoir 260 to the SPE cartridge 252 or delivery fluid from the syringe pump 306 to the SPE cartridge 252. Waste valve 318 is used to divert fluid from the SPE cartridge 252 either to waste or the final product container 250. Cleaning valve 320 is used to send pressurized inert gas (e.g., nitrogen) through various lines for cleaning the purification and formulation device 200. Fraction collection valve 322 is used to divert fractions to either the fraction tubes 270 to the dilution reservoir 260 for subsequent formulation, or to one of the waste ports 292 on the back of the unit. Pressure release valve 324 is used to permit the passage of air during the filling of the dilution reservoir 260 with liquid. In addition, pressure release valve 324 is also connected to pressurized inert gas which is used to push fluid out of the dilution reservoir 260 and onto the SPE cartridge 252 during the formulation process.

FIG. 8 illustrates a schematic layout of the flow paths in the purification and formulation device 200. The formulation subsystem 204 is illustrated by the dashed line in FIG. 8 while the purification subsystem 202 includes the remaining components and processes. As seen in FIG. 8, the injection valve 240 is coupled at one port to the HPLC pump 218 via stainless steel tubing (or other type of tubing) which delivers the carrier/mobile phase used for the HPLC separation process. Multiple different carrier/mobile phases can be run through the HPLC pump 218 as well as mixtures of the same. FIG. 9 illustrates an enlarged view of the injection valve 240. The injection valve 240 is coupled at another port to a first sample input 340 which, in one embodiment, is the output line from the radiosynthesizer 100 from a first cassette 102. The injection valve 240 is coupled at another port to a second sample input 342 which, in one embodiment, is the output line from the radiosynthesizer 100 from a second cassette 102. Liquid sensors 274, 276 are located in respective fluid lines that connect each cassette 102 to the ports on the injection valve 240. A first sample loop 344 is connected to two ports on the injection valve 240 which is used to hold sample from the first sample input 340. A second sample loop 346 is connected to two ports on the injection valve 240 which is used to hold sample from the second sample input 342. The sample loops 344, 346 can contain set volumes of fluid, for example, 5 mL of sample. The two sample loops 344, 346 permit two different purifications runs to be run on the purification and formulation device 200. The injection valve 240 is a two-position valve; when one sample loop (e.g., 344) is in the "load" position, the other loop (e.g., 346) is in the "inject." Actuation of the injection valve 240 reverses the respective load and injection positions for the sample loops 344, 346. As best seen in FIG. 9, the second loop 346 is in the "load" position while the first loop 344 is in the "inject" position. Note that in an alternative embodiment, sample may be injected into a sample loop 344, 346 manually via input lines 340, 342 using a syringe or the like.

The injection valve 240 is also coupled to two waste lines 348, 350 that direct fluid contained therein to waste containers or receptacles 352. The injection valve 240 further includes an output line 354 (e.g., stainless steel) that is connected to the input of the column selector valve 242. The column selector valve 242 is able to connect one of a plurality of columns 243 that may be loaded into the device into the fluid path of the instrument.

Still referring to FIG. 8, after fluid passes through the columns, it enters the UV detector 300 followed by the radiation detector 302. The fluid then passes through the cleaning valve 320 that passes the fluid to the fraction collection valve 322 whereby fractions may be collected in fraction tubes 270. Fraction collection valve 322 also includes a waste line 356 that is connected to a waste container or receptacle 357 via waste ports or fittings 292. The fraction collection valve 322 also includes a product line 358 that diverts product to the dilution reservoir 260 which is already pre-loaded or filled with a volume of high-purity water by the user (capacity is 100 ml) into which the product will become diluted. The dilution reservoir 260 also contains an output line 360 that extends into the bottom of the dilution reservoir 260 and is connected at the other end to the cartridge valve 316. The outlet of the cartridge valve 316 is connected to an output line 362 that delivers fluid to the SPE cartridge 252 via port 256. Fluid exits the SPE cartridge 252 and then passes through port 258. The other inlet of the cartridge valve 316 is coupled to the output line 363 of the syringe pump 306.

The syringe pump 306 is a six (6) port syringe pump with another port connected to waste line 364 that connects to a waste container or receptacle 358 via waste ports or fittings 292. Another port of the syringe pump 306 connects to an input line 366 that connects to a container or receptacle 368 that contains water. Another port of the syringe pump 306 connects to an input line 370 that connects to a container or receptacle 372 that contains a saline solution. Still another port of the syringe pump 306 connects to an input line 374 that connects to a container or receptacle 376 that eluting fluid (e.g., ethanol or EtOH). Another port of the syringe port 306 is connected to an input line 378 that is open to air 380 that is used to push residual fluid in the fluid carrying lines when product is sent back to the radiosynthesizer 100 for additional unit operations. A sterile air filter 381 may be interposed between the air source 380 and the input to the syringe pump 306.

The SPE cartridge 252 is coupled to the waste valve 318 via output line 382. The waste valve 318 includes a waste line 384 that connects to the waste container or receptacle 386 via waste ports or fittings 292. The waste valve 318 is also coupled to an output line 388 that delivers product to the final product container 250. The final product container 250 may include a sterile vial containing a septum which is penetrated by a needle or the like that is secured to a sterile filter 390. The final product container 250 may be contained in a lead pig 251 that limits the emission of radiation. As illustrated in FIG. 8, a vent line 392 is provided along with a sterile filter 394 so that air contained in the final product container 250 can vent out when liquid is delivered to the final product container 250.

A pressure regulated inert gas source 400 (e.g., nitrogen) is seen in FIG. 8 connected to the cleaning valve 320 and the pressure release valve 324. As explained herein, the pressurized inert gas source 400 delivers inert gas to the dilution reservoir 260 to push liquid containing the radiopharmaceutical compound into the output line 360 when the pressure release valve 324 is activated. The pressurized inert gas source 400 further is used to clean various fluid lines by passing drying inert gas via cleaning valve 320 during a cleaning procedure.

Figure 10:
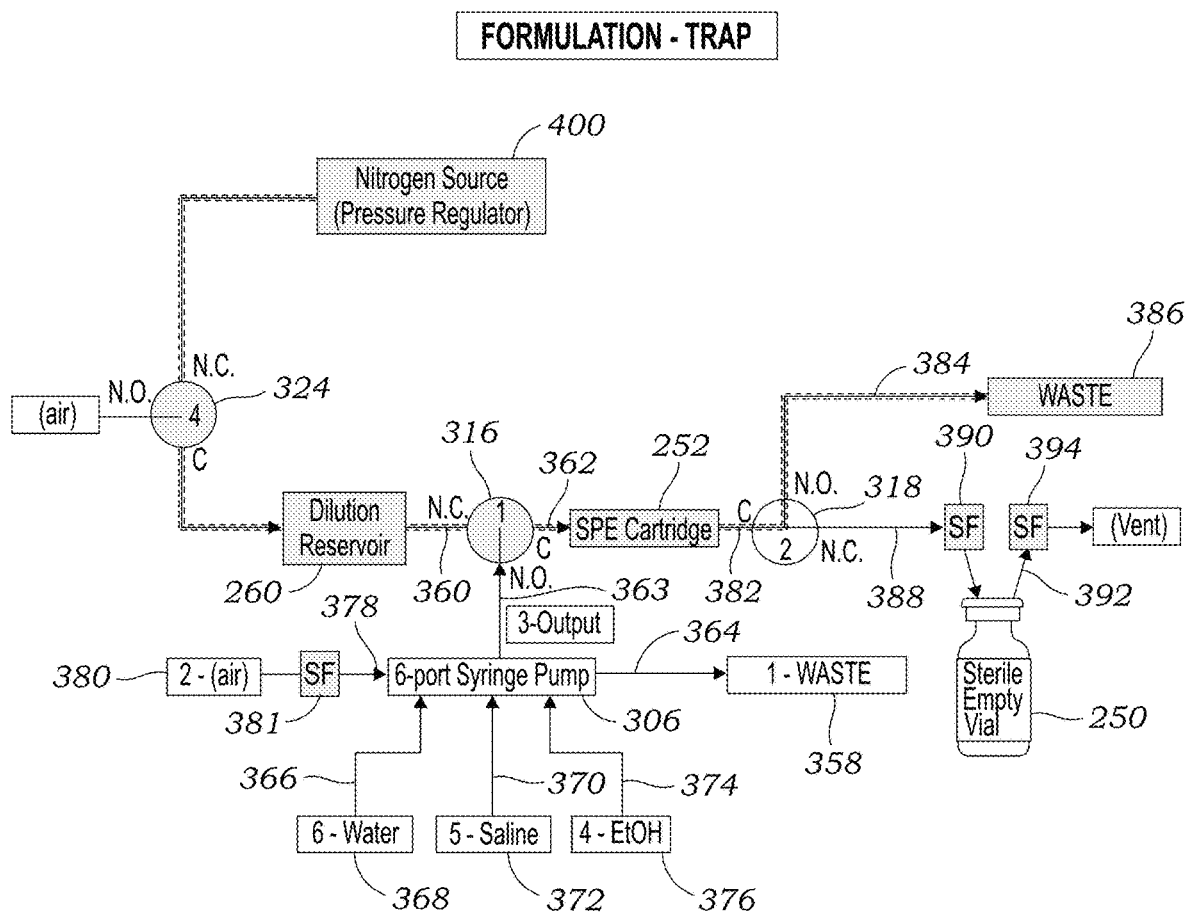
FIG. 10 illustrates the flow path utilized in the FORMULATION: TRAP operation. The thick, darkened lines illustrate the flow path for this particular unit operation.
Figure 11:
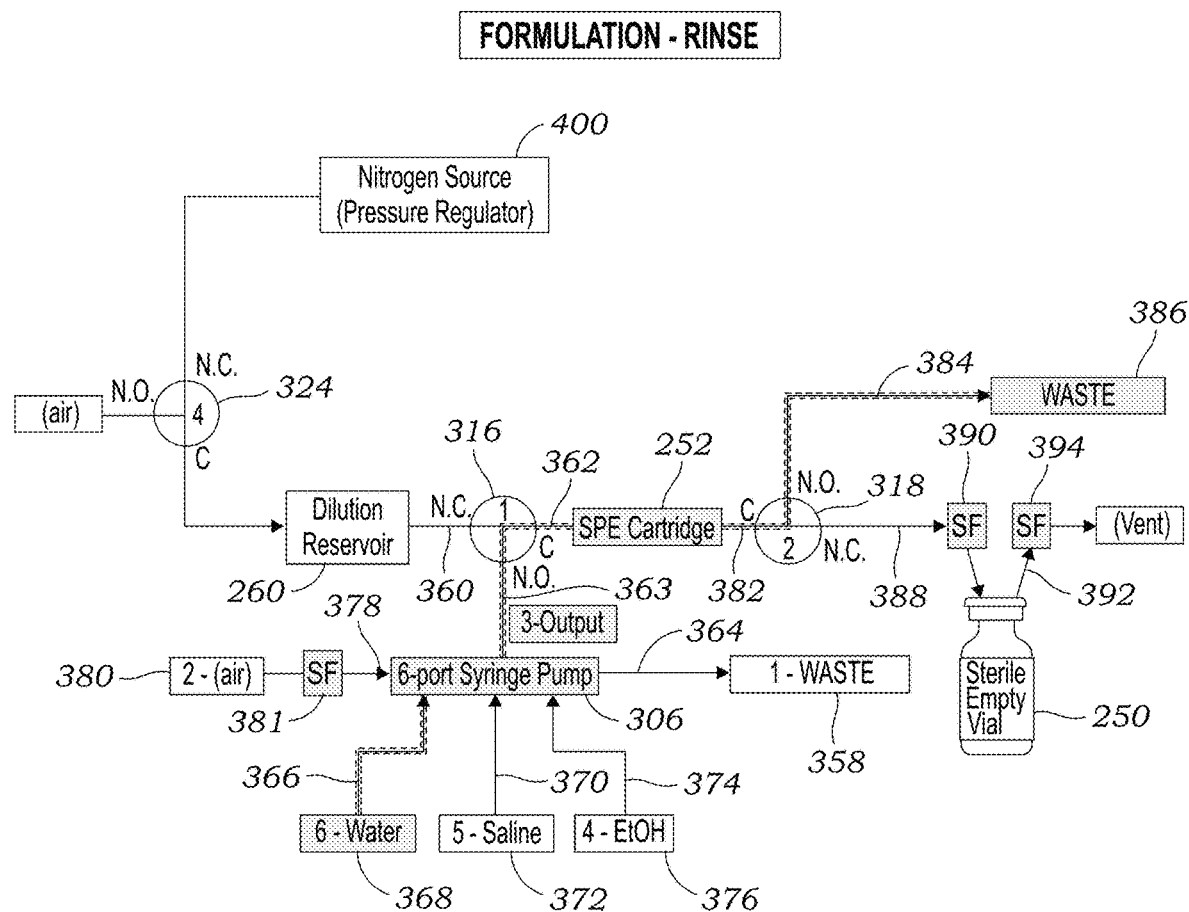
FIG. 11 illustrates the flow path utilized in the FORMULATION: RINSE operation. The thick, darkened lines illustrate the flow path for this particular unit operation.
Figure 12:
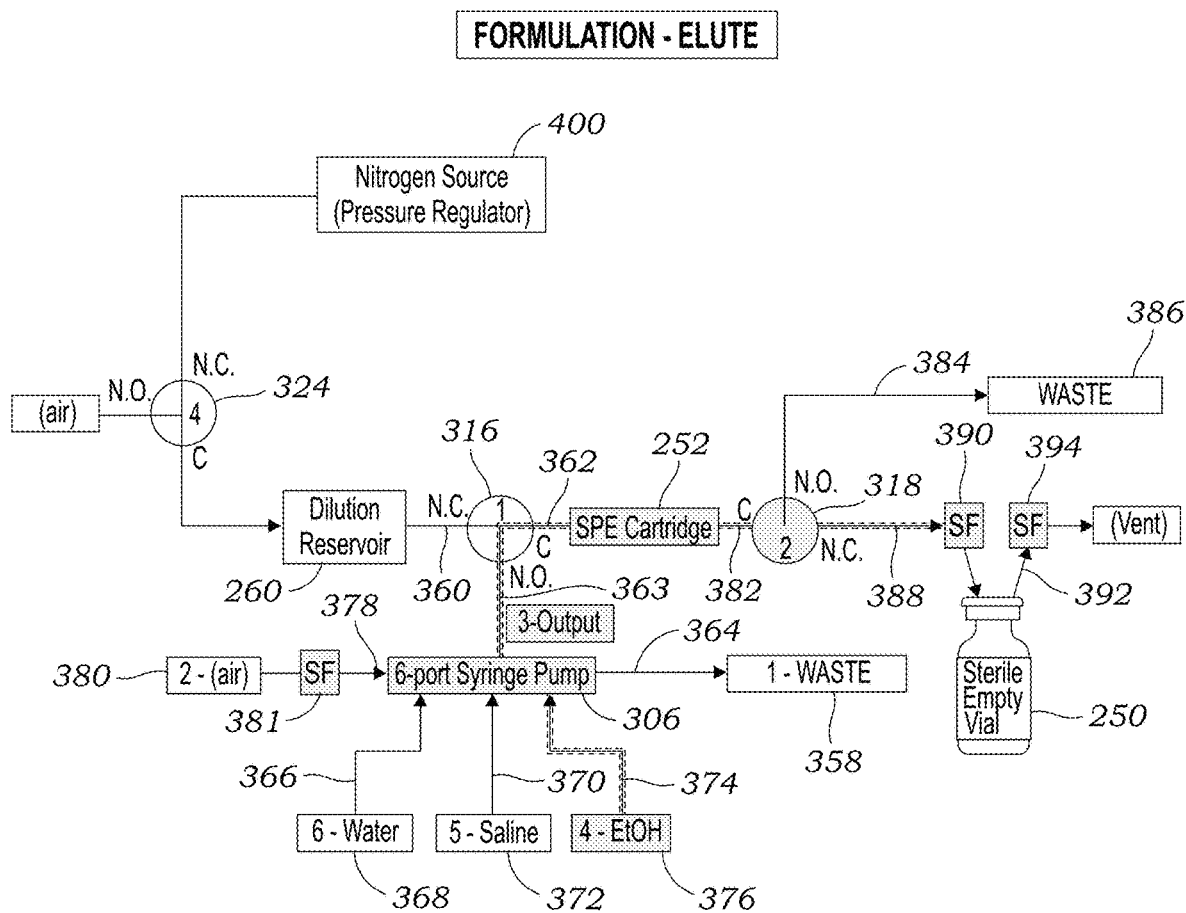
FIG. 12 illustrates the flow path utilized in the FORMULATION: ELUTE operation. The thick, darkened lines illustrate the flow path for this particular unit operation.
Figure 13:
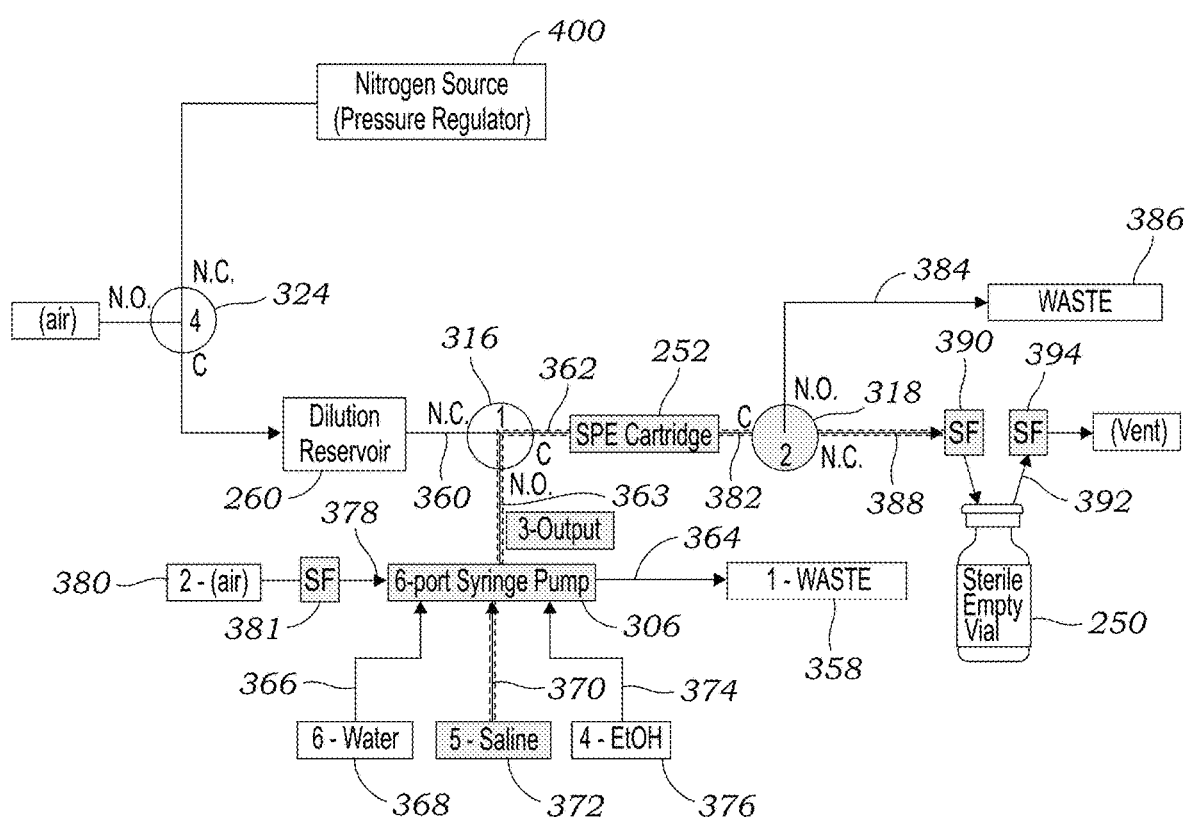
FIG. 13 illustrates the flow path utilized in the FORMULATION: RECONSTITUTE operation. The thick, darkened lines illustrate the flow path for this particular unit operation.

FIGS. 10-13 illustrate the schematic layout of the flow paths used in the four (4) step FORMULATION unit operations. These include FORMULATION: TRAP (FIG. 10); FORMULATION: RINSE (FIG. 11); FORMULATION: ELUTE (FIG. 12); FORMULATION: RECONSTITUTE (FIG. 13). As seen in FIG. 10, in the FORMULATION: TRAP operation, the pressure release valve 324 and the cartridge valve 316 are actuated so that pressurized inert gas from pressure regulator 400 enters the dilution reservoir 260 and pushes liquid containing the radiopharmaceutical compound into the output line 360 where it enters line 362 and into the SPE cartridge 252 whereby the radiopharmaceutical compound becomes "trapped" on the solid phase sorbent material contained therein (e.g., resin). The waste valve 318 is positioned to divert fluid the line 384 and waste container or receptacle 386. Next, with reference to FIG. 11, in the FORMULATION: RINSE operation, the syringe pump 306 is activated to pump water from container or receptacle 368 into output lines 366, 363. The cartridge valve 316 is actuated to pass the water into line 362 where the contents of the SPE cartridge 252 are washed with water. This removes impurities and cleans the fluid lines of organic solvents. The waste valve 318 is positioned to divert fluid the line 384 and waste container or receptacle 386. The volume of rinsing solution may be adjusted using the software 222 on the computing device 208.

Next, with reference to FIG. 12, in the FORMULATION: ELUTE operation, the syringe pump 306 is activated to pump eluting fluid (e.g., EtOH) from the container or receptacle 376 into output lines 374, 363. The cartridge valve 316 is actuated to pass the eluting fluid into line 362 where the radiopharmaceutical compound that is trapped in the SPE cartridge 252 elutes off the solid phase sorbent material and into the eluting liquid. The waste valve 318 is actuated to pass this eluting fluid into output line 388 where is passes through the sterile filter 390 and into the final product container 250.

Next, with reference to FIG. 13, in the FORMULATION: RECONSTITUTE operation, the syringe pump 306 is activated to pump a saline solution or fluid (e.g., phosphate buffered saline) from the container or receptacle 372 into output lines 370, 363. The cartridge valve 316 is actuated to pass the saline solution or other buffered aqueous solution into line 362 and through the SPE cartridge 252. The waste valve 318 is actuated to pass this saline solution into output line 388 where is passes through the sterile filter 390 and into the final product container 250. This step of the FORMULATION operation allows any residual organic solvents or other unwanted compounds to be diluted to an acceptable level so that the radiopharmaceutical compound is ready for use. Importantly, the syringe pump 306 never encounters any crude or purified product or any of the solvents that may be involved in the TRAP operation. The syringe pump 306 is only programmed to use the fluid path 363 as the output line; it never aspirates fluid through this line.

In the embodiment where the output of the product from the output line 388 is returned back to a cartridge 102 of the radiosynthesizer 100, the source of air 380 is pumped by the syringe pump 306 through the sterile filter 381 and into the downstream lines 363, 388 to chase the ethanol or other eluting fluid through the lines.

The purification and formulation device 200 may also utilize an automated cleaning operation for both the purification 202 and formulation 204 flow paths. In the purification cleaning operation, a mobile phase is pumped by an HPLC pump 218 through the injector valve 240, column selector valve 242, column(s) 243, UV detector 300, radiation detector 302, cleaning valve 320, fraction collection valve 322, product line 358, waste line 356, and the lines (e.g., four) connected to the fraction containers 270. The mobile phase is collected the dilution reservoir 260 as well as fraction containers 270. After a programmed amount of time, the HPLC pump 218 turns off. The cleaning valve 320 then activates and the pressure regulator 400 outputs compressed inert gas for a programmed time and at a programmed pressure. The fraction collection valve 322 cycles between all outputs (described above) to thoroughly dry the lines. The formulation clean operation cleans the valves and lines used in the FORMULATION operations (FIGS. 10-13). In this process, the dilution reservoir 260 is filled with ethanol (e.g., 100 mL) and the saline line 370 and water line 366 are placed in a waste container. A cleaning solution (e.g., ethanol) in the container or receptacle 376 is also used to complete the cleaning process. The final product line 388 is also placed in a waste container. The SPE cartridge 252 is removed and the input/output fittings 256, 258 are connected together. In the cleaning operation, the syringe pump 306 aspirates the cleaning solution or air to rinse and dry all formulation subsystem 204 fluid paths. Again, both cleaning operations may be performed automatically by the controller 206.

FIG. 14 illustrates an example of the GUI 222 that is displayed to the user on the computing device 208. In this example, the user is given current information from the purification subsystem 202 regarding a current purification process being run on the purification and formulation device 200. In this example, the GUI 222 includes a navigation button 500 as well as indicates which subsystem is selected (i.e., purification subsystem 202 or formulation 204 subsystem) by indicator 502 (in FIG. 14 purification is selected but for formulation, indicator 502 will be moved to indicate selection of the formulation operation as seen in FIG. 15). The GUI 222 provides the user with the selected pathway of the fraction collection valve 322 (i.e., product line 358, fraction 270, or waste 356). In this example, the fraction collection valve 322 is diverting product as seen by highlighted selection 504. The GUI 222 further includes a graphing screen 506 that provides live data from the UV detector 300 and/or the radiation detector 302. Various graphing options are provided as seen in option menu 508. These options include AU (for UV graphs), mV (for radiation graphs), output overlay, record, clear, and zero. The GUI 222 also provides a panel of information 510 for control and feedback. This panel 510 displays current operational conditions and configurations of the purification subsystem 202.

During operation of the device 200 by the user, various fractions that are separated in the purification subsystem may be selected by the user using a touch button found on the GUI 222 such that the particular fraction is delivered to the fraction collection tubes or vials 270 or delivered as the product to the dilution reservoir 260. This is a process whereby fractions are manually selected by the user. In another alternative embodiment, the software itself can be programmed to automatically select various fractions for shunting to either the collection tubes or vials 270 or the main product line 358. Automated control of the fraction collection valve 322 may look to real time or near real time data generated by the UV detector 300 and radiation detector 302 as well as known elapsed elution times of purified product from the columns 243 to identify suspect or desired fractions of interest. Peak detection algorithms may look at designated time windows and/or set threshold values for the output of UV and/or radiation peaks which can then be used to trigger actuation of the fraction collection valve 322.

FIG. 15 illustrates an example of the GUI 222 that is displayed to the user on the computing device 208 when the formulation subsystem 204 is selected by the user as indicated by indicator 502. In FIG. 15, a step selection menu 512 is provided to the user to program and monitor various aspects of the formulation operation. This includes the TRAP operation, the RINSE operation, the ELUTE operation, and the RECONSTITUTE operation. As seen in FIG. 15, the user is provided with a control window 514 that can be used to adjust various operational parameters via edit button 516. GUI 222 also illustrates a live video image 518 of the dilution reservoir 260 taken with camera 314.

Figure 16:
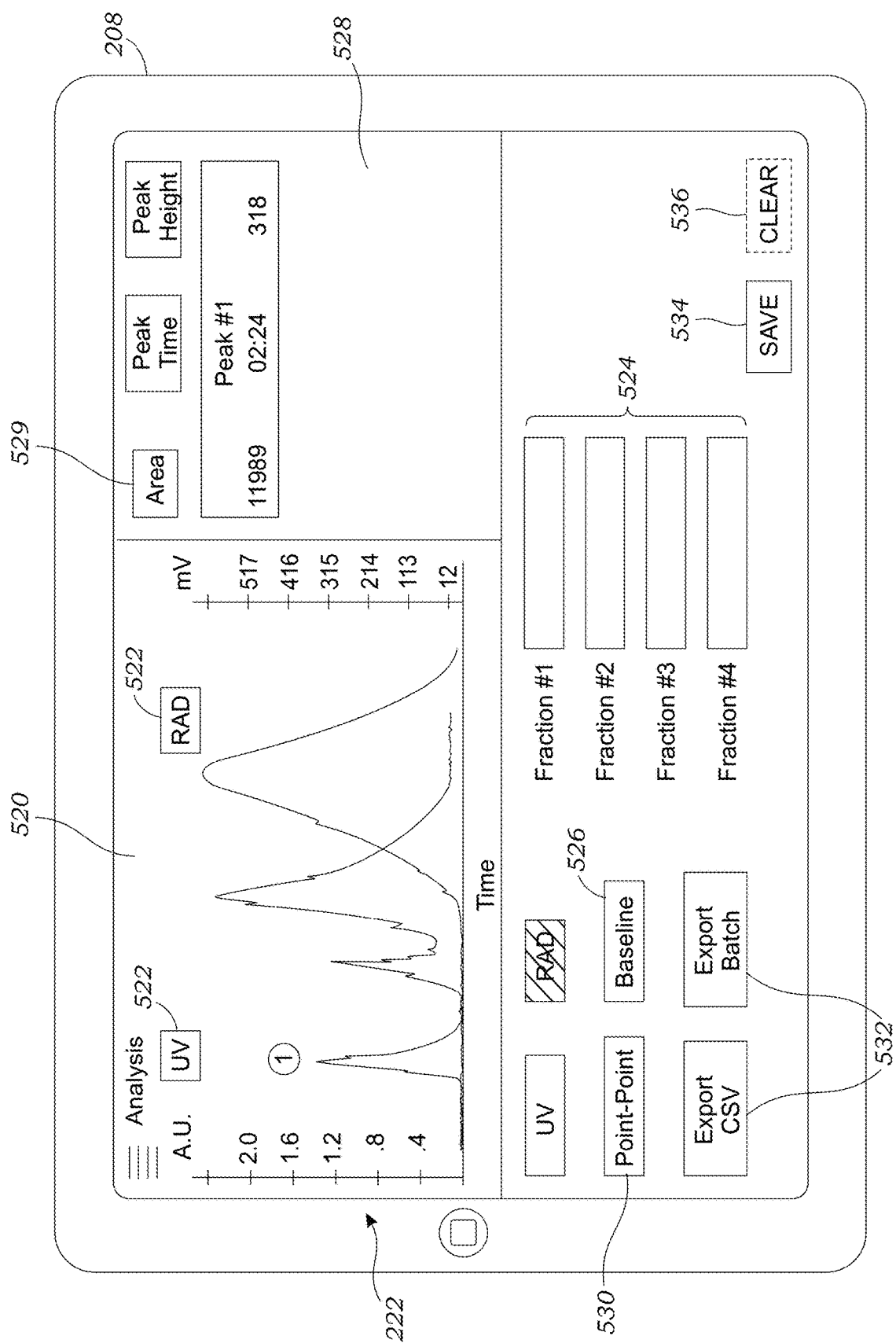
FIG. 16 illustrates an example of the GUI that is used for data analysis.

FIG. 16 illustrates another example of the GUI 222 that is displayed to the user on the computing device 208 and used for data analysis. As seen in FIG. 16 a graph window 520 is provided that is used to display UV data, radiation data, or both. Buttons 522 are selected or deselected to display or hide the desired data. Fractions, if not already named, can be manually named using fraction naming fields 524. The GUI 222 also provides the user the ability to analyze various peaks present in the data fields. For example, the user is able to perform a baseline peak area calculation using baseline button 526. In this example, the radiation detector data is analyzed for peak #1. After identifying the peak and baseline, the software automatically calculates peak area, peak time, and peak height which are displayed in peak output window 528. Peak area may also be expressed as a percentage of the total area, for example, by depressing the area button 529 (which toggles between absolute and percentage values). Point-to-point calculation for peak areas is performed using the point-point button 530 as illustrated in FIG. 16. In peak-to-peak calculation two points are defined that define a line to which the peak is integrated. Data can be exported using export buttons 532 (e.g., batch data or raw .CSV data). Analysis data may be saved or cleared using save button 534 and clear button 536.

While embodiments of the present invention have been shown and described, various modifications may be made without departing from the scope of the present invention. For example, while the invention has been described as being usable with the ELIXYS radiosynthesizer available from Sofie Biosciences, the invention is not limited to any particular model or brand. In addition, while the purification and formulation device has been described as including two sample loops, in other embodiments the device may include more than two loops or even a single loop. The invention, therefore, should not be limited except to the following claims and their equivalents.

What is claimed is:

1. A device for purifying and formulating a radiopharmaceutical compound comprising:
   an automated purification subsystem comprising
      a computer controlled injection valve coupled to a high performance liquid chromatography (HPLC) pump, a plurality of sample loops, and an output line from the injection valve, the computer controlled injection valve having one or more ports configured to receive an input fluid containing the radiopharmaceutical compound, wherein one of the plurality of sample loops is connected to the HPLC pump and the output line from the injection valve and another sample loop of the plurality of sample loops is connected to a port configured to receive the input fluid;
      an automated column selector valve coupled to the output line from the injection valve and configured to select one of a plurality of columns for fluid to pass through;
      one or more detectors configured to receive an output of the selected column, the one or more detectors comprising at least a radiation detector;
      a downstream fraction selector valve disposed downstream with respect to the one or more detectors and configured to divert fluid flow to one of a product output, waste output, and fraction output; and
   an automated formulation subsystem coupled to the product output of the downstream fraction selector valve, the automated formulation subsystem comprising:
      a dilution reservoir pre-loaded or filled with a volume of dilution solvent and configured to receive a product fraction from the downstream fraction selector valve, the dilution reservoir fluidically coupled to a solid-phase extraction cartridge;
      a computer controlled pump coupled to a plurality of different fluid reagents that include a wash solution, a saline solution, and an eluting solution, the computer controlled pump configured to pump selected fluid reagents through the solid-phase extraction cartridge via a computer controlled cartridge valve interposed between the dilution reservoir and the solid-phase extraction cartridge; and
      a final output line fluidically coupled to an output of the solid-phase extraction cartridge, wherein a computer controlled waste valve is coupled to the final output line to divert fluid flow to waste or the final output line; and
      a computer accessible controller interfacing with the automated purification subsystem and the automated formulation subsystem, wherein one or more operations of the automated purification subsystem and the automated formulation subsystem, and the controller are programmable by a user.

2. The device of claim 1, further comprising a final product container, wherein the final output line is coupled to the final product container.

3. The device of claim 1, wherein the final output line or an output line from the fraction selector valve is coupled to radiosynthesizer device.

4. The device of claim 1, wherein the computer controlled injection valve comprises a two-position valve, and wherein in a first position, a first sample loop is connected to the HPLC pump and the output line from the injection valve and a second sample loop is connected to the port configured to receive the input fluid, and wherein in a second position the second sample loop is connected to the HPLC pump and the output line from the injection valve and the first sample loop is connected to the port configured to receive the input fluid.

5. The device of claim 1, wherein the plurality of columns are mounted in respective column holders in the device.

6. The device of claim 1, wherein the one or more detectors comprise a UV detector and a radiation detector.

7. The device of claim 1, further comprising a camera positioned to obtain live images of the dilution reservoir.

8. The device of claim 1, wherein the computer controlled pump coupled to a plurality of different fluid reagents comprises a multi-port syringe pump.

9. The device of claim 1, further comprising a compressed source of inert gas, the compressed source of inert gas fluidically coupled to the dilution reservoir via an automated valve, wherein the compressed source of inert gas pushes fluid contained in the dilution reservoir into the solid-phase extraction cartridge.

10. The device of claim 1, wherein the computer accessible controller controls one or more of the injection valve, the HPLC pump, the column selector valve, the downstream fraction selector valve, the pump coupled to a plurality of different fluid reagents, the cartridge valve, and the waste valve.

11. The device of claim 10, wherein the controller is programmed to automatically actuate a downstream fraction selector valve based on readings obtained from the one or more detectors.

12. The device of claim 11, wherein the controller is programmed to automatically actuate the downstream fraction selector valve to collect a compound in either the fraction output or product output based on automated peak detection based on designated time windows and/or set threshold values for the one or more detectors.

13. A system for the formation, purification, and formulation of a radiopharmaceutical compound comprising:
a radiosynthesizer device configured for synthesizing radiopharmaceutical compound;
an automated purification subsystem comprising
a computer controlled injection valve coupled to a high performance liquid chromatography (HPLC) pump, one or more sample loops, and an output line from the injection valve, the computer controlled injection valve having one or more ports configured to receive an input fluid containing the radiopharmaceutical compound from the radiosynthesizer device, wherein one of sample loops is connected to the HPLC pump and the output line from the injection valve;
an automated column selector valve coupled to the output line from the injection valve and configured to select one of a plurality of columns for fluid to pass through;
one or more detectors configured to receive an output of the selected column, the one or more detectors comprising at least a radiation detector;
a downstream fraction selector valve disposed downstream with respect to the one or more detectors and configured to divert fluid flow to one of a product output, waste output, and fraction output; and
an automated formulation subsystem coupled to the product output of the downstream fraction selector valve, the automated formulation subsystem comprising:
a dilution reservoir configured to receive a product fraction from the downstream fraction selector valve, the dilution reservoir fluidically coupled to a solid-phase extraction cartridge;
pumping means configured to push fluid contents contained in the dilution reservoir into the solid-phase extraction cartridge in response to actuation of the automated valve;
a computer controlled pump coupled to a plurality of different fluid reagents and configured to pump selected fluid reagents through the solid-phase extraction cartridge via a computer controlled cartridge valve interposed between the dilution reservoir and the solid-phase extraction cartridge;
a final output line fluidically coupled to an output of the solid-phase extraction cartridge, wherein a computer controlled waste valve is coupled to the final output line to divert fluid flow to waste or the final output line; and
a computer accessible controller interfacing with the radiosynthesizer device, the automated purification subsystem, and the automated formulation subsystem, wherein one or more operations of the automated purification subsystem, the automated formulation subsystem, and the controller are programmable by a user.

14. The system of claim 13, wherein the controller is programmable using a separate computing device.

15. The system of claim 13, wherein the final output line is coupled to a final product container.

16. The system of claim 13, wherein the controller is programmed with a program configured to (i) load the input fluid into one of the sample loops, (ii) select one of the plurality of columns with the automated column selector valve, (iii) inject the input fluid into the selected column with the computer controlled injection valve, (iv) diverting a product fraction to the automated formulation subsystem with the downstream fraction selector valve and collected in the dilution reservoir.

17. The system of claim 16, wherein the controller is programmed with a program comprising a trap operation followed by a rinse operation and elute operation to push fluid from the dilution reservoir through the solid-phase extraction cartridge followed sequentially by pumping of wash fluid and an eluting solution, wherein the programmed controller diverts the wash fluid exiting the solid-phase extraction cartridge to a waste line and transfers the eluting solution exiting the solid-phase extraction cartridge to a final product container coupled to the final output line.

18. The system of claim 17, wherein the controller is programmed with a program comprising a reconstitute operation to pump a saline or aqueous solution through the solid-phase extraction cartridge and into the final product container coupled to the final output line.

19. A method of using the system of claim 14, comprising:
generating a sequence of operations to be performed by the radiosynthesizer device, the automated purification subsystem, and the automated formulation subsystem using a graphical user interface on the computing device to select a series of pre-set unit operations to be performed; and
running the radiosynthesizer device, the automated purification subsystem, and the automated formulation subsystem in accordance with the selected series of pre-set operations to be performed.

20. The method of claim 19, wherein an automated cleaning operation is performed on the purification subsystem and the automated formulation subsystem.

* * * * *